US011332543B2

(12) United States Patent
Tran et al.

(10) Patent No.: US 11,332,543 B2
(45) Date of Patent: May 17, 2022

(54) ANTIBODY POLYPEPTIDES AND USES THEREOF

(71) Applicant: FREDAX AB, Bjarred (SE)

(72) Inventors: Amanda Thuy Tran, Malmo (SE); Anders Axelsson, Bjärred (SE); Cecilia Ann-Christin Malmborg Hager, Helsingborg (SE); Kjell Sjöström, Lund (SE); Sven-Erik Strand, Lund (SE); Urpo Juhani Lamminmäki, Vanhalinnna (SE)

(73) Assignee: FREDAX AB, Bjarred (SE)

( * ) Notice: Subject to any disclaimer, the term of this patent is extended or adjusted under 35 U.S.C. 154(b) by 160 days.

(21) Appl. No.: 15/761,260

(22) PCT Filed: Oct. 4, 2016

(86) PCT No.: PCT/EP2016/073684
§ 371 (c)(1),
(2) Date: Mar. 19, 2018

(87) PCT Pub. No.: WO2017/060247
PCT Pub. Date: Apr. 13, 2017

(65) Prior Publication Data
US 2018/0273634 A1 Sep. 27, 2018

(30) Foreign Application Priority Data

Oct. 5, 2015 (GB) .................................... 1517550
Oct. 29, 2015 (GB) .................................... 1519105

(51) Int. Cl.
*A61K 39/00* (2006.01)
*C07K 16/30* (2006.01)
*A61K 51/10* (2006.01)
*A61K 39/395* (2006.01)
*A61K 47/68* (2017.01)
*A61P 35/00* (2006.01)
*G01N 33/574* (2006.01)

(52) U.S. Cl.
CPC ........ *C07K 16/3069* (2013.01); *A61K 39/395* (2013.01); *A61K 47/6803* (2017.08); *A61K 47/6869* (2017.08); *A61K 51/1072* (2013.01); *A61K 51/1096* (2013.01); *A61P 35/00* (2018.01); *G01N 33/57434* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/569* (2013.01); *C07K 2317/622* (2013.01); *C07K 2317/624* (2013.01); *C07K 2317/92* (2013.01); *C07K 2317/94* (2013.01)

(58) Field of Classification Search
CPC ................................................ A61K 2039/505
See application file for complete search history.

(56) References Cited

U.S. PATENT DOCUMENTS

| 4,235,871 A | 11/1980 | Papahjopoulos et al. |
| 5,851,451 A | 12/1998 | Takechi et al. |
| 2014/0286862 A1* | 9/2014 | Strand ................ A61K 51/1072 424/1.49 |
| 2016/0317683 A1* | 11/2016 | Strand ................ A61K 51/1072 |

FOREIGN PATENT DOCUMENTS

| EP | 0213303 B1 | 9/1991 | |
| GB | 2520353 A | 5/2015 | |
| JP | 2010/004895 A | 1/2010 | |
| RU | 2537263 C2 | 5/2014 | |
| WO | 2006/072620 A1 | 7/2006 | |
| WO | 2006087374 A1 | 8/2006 | |
| WO | 2010/009124 A2 | 1/2010 | |
| WO | 2013061083 A2 | 5/2013 | |
| WO | WO-2013061083 A2 * | 5/2013 | ....... G01N 33/57434 |
| WO | 2015148979 A1 | 10/2015 | |

OTHER PUBLICATIONS

Heuzé-Vourc'h et al. (Eur. J. Biochem. Feb. 2003; 270 (4): 706-14).*
Pettersen et al. (J. Immunol. Jun. 15, 1999; 162 (12): 7031-7040).*
Jiang et al. (J. Biol. Chem. Feb. 11, 2005; 280 (6): 4656-4662).*
Riemer et al. (Mol. Immunol. 2005; 42: 1121-1124).*
Campbell et al. (Blood Reviews. 2003; 17: 143-152).*
Kipps et al. (J. Exp. Med. Jan. 1, 1985; 161 (1): 1-17).*
Takeshita et al. (Leukemia. Jul. 2009; 23 (7): 1329-36).*
Henry et al. (Cancer Res. Nov. 1, 2004; 64: 7995-8001).*
McDevitt et al. (Cancer Res. Nov. 1, 2000; 60: 6095-6100).*
Yamaguchi et al. (Biochem. Biophys. Res. Commun. Nov. 1, 2014; 454 (4): 600-603).*
Barbas, et al., "Assembly of combinatorial antibody libraries on phage surfaces: The gene III site" Proc. Natl. Acad. Sci. USA (1991) 88:7978-7982.
Almagro, et al., "Humanization of antibodies" Frontiers in Bioscience (2008) 13:1619-1633.
Sklar, et al., "Flow cytometric analysis of ligand-receptor interactions and molecular assemblies" Annu Rev Biophys Biomol Struct. (2002) 31:97-119.

(Continued)

*Primary Examiner* — Stephen L Rawlings
(74) *Attorney, Agent, or Firm* — Robert C. Netter, Jr.; Dann, Dorfman, Herrell & Skillman

(57) ABSTRACT

The present invention provides antibody polypeptides with binding specificity for prostate specific antigen (PSA), wherein the antibody polypeptide comprises (a) a heavy chain variable region comprising the amino acid sequences of SEQ ID NO:1 and SEQ ID NO:2 and SEQ ID NO:3 and/or (b) a light chain variable region comprising the amino acid sequences of SEQ ID NO:4 and SEQ ID NO:5 and SEQ ID NO:6, and wherein the heavy chain variable region and light chain variable region comprise framework amino acid sequences from one or more human antibodies. The invention further provides use of said antibody polypeptides in the diagnosis and treatment of prostate cancer.

22 Claims, 5 Drawing Sheets

Figure 1:
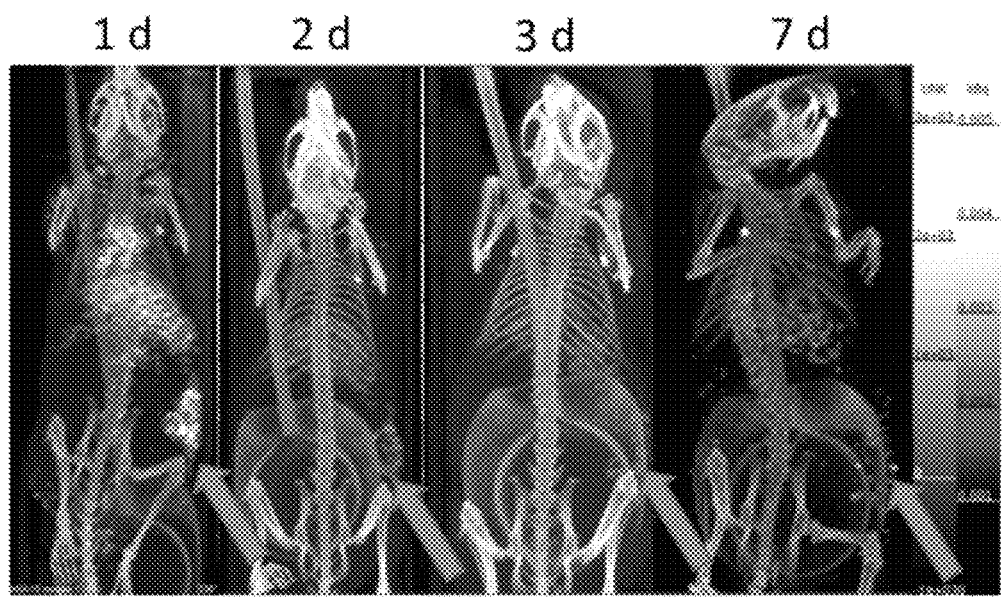

Specification includes a Sequence Listing.

(56) References Cited

OTHER PUBLICATIONS

Huang, et al., "A Time-Efficient, Linear-Space Local Similarity Algorithm" Adv. Appl. Math. (1991) 12:337-357.

Thompson, et al., "Clustal W: improving the sensitivity of progressive multiple sequence alignment through sequence weighting, position-specific gap penalties and weight matrix choice" Nucleic Acids Research (1994) 22(22):4673-4680.

Meziere, et al., "In Vivo T Helper Cell Response to Retro-Inverso Peptidomimetics" J. Immunol. (1997) 159 (7):3230-3237.

Veber, et al., "Conformationally restricted bicyclic analogs of somatostatin" Proc. Natl. Acad. Sci. (1978) 75 (6):2636-2640.

Angov "Codon usage: Nature's roadmap to expression and folding of proteins" Biotechnol. J. (2011) 6:650-659.

Lilja, et al., "Prostate-Specific Antigen in Serum Occurs Predominantly in Complex with a1-Antichymotrypsin" Clin. Chem. (1991) 37(9):1618-1625.

Strand, et al., "Pharmacokinetic modeling" Med Phys. (1993) 20(2 Pt 2):515-27.

Bardies, et al., "Quantitative imaging for clinical dosimetry" Nuclear Instruments and Methods in Physics Research A (2006) 569:467-471.

Sjogreen-Gleisner, et al., "Dosimetry in patients with B-cell lymphoma treated with [(90)Y]ibritumomab tiuxetan or [(131)I]tositumomab" J. Nucl. Med. Mol. Imaging (2011) 55:126-154.

Sjogreen, et al., "The LundADose method for planar image activity quantification and absorbed-dose assessment in radionuclide therapy" Cancer Biother. Radiopharm. (2005) 20:92-97.

Garkavij, et al., "177Lu-[DOTA0,Tyr3] octreotate therapy in patients with disseminated neuroendocrine tumors: Analysis of dosimetry with impact on future therapeutic strategy" Cancer (2010) 116:1084-1092.

Harris, L.J., et al., "Comparison of Intact Antibody Structures and the Implications for Effector Function" Adv. Immun. (1999) 72:191-208.

Evans-Axelsson, S., et al. "Targeting Free Prostate-Specific Antigen for in vivo imaging of prostate cancer using a monoclonal antibody specific for unique epitopes accessible on free Prostate-Specific Antigen alone" Cancer Biotherapy Radiopharmaceuticals (2012) 27(4):243-251.

De Lorenzo-Caceres Ascanio, A., "Afortunadamente No. tiene usted nada" Atencion primaria (2001) 27 (4):284-285.

Su, et al. "Gene construction, expression and identification of human-derived anti-prostate specific membrane antigen single chain antibody" Zhonghua Nan Ke Xue (2014) 20(12):1063-7 [ABSTRACT only].

\* cited by examiner

SEQUENCE LISTING

```
<160> NUMBER OF SEQ ID NOS: 24

<210> SEQ ID NO 1
<211> LENGTH: 7
<212> TYPE: PRT
<213> ORGANISM: Artificial Sequence
<220> FEATURE:
<223> OTHER INFORMATION: Heavy chain variable region CDRH1

<400> SEQUENCE: 1

Thr Thr Gly Met Gly Val Ser
1               5

<210> SEQ ID NO 2
<211> LENGTH: 15
<212> TYPE: PRT
<213> ORGANISM: Artificial Sequence
<220> FEATURE:
```

```
<223> OTHER INFORMATION: Heavy chain variable region CDRH2

<400> SEQUENCE: 2

His Ile Tyr Trp Asp Asp Lys Arg Tyr Ser Thr Ser Leu Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Heavy chain variable region CDRH3

<400> SEQUENCE: 3

Lys Gly Tyr Tyr Gly Tyr Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Light chain variable region CDRL1

<400> SEQUENCE: 4

Arg Ala Ser Gln Asn Val Asn Thr Asp Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Light chain variable region CDRL2

<400> SEQUENCE: 5

Ser Thr Ser Tyr Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Light chain variable region CDRL3

<400> SEQUENCE: 6

Gln Gln Tyr Ser Asn Tyr Pro Leu Thr
1               5

<210> SEQ ID NO 7
<211> LENGTH: 244
<212> TYPE: PRT
<213> ORGANISM: Homo sapiens
<220> FEATURE:
<223> OTHER INFORMATION: Amino acid sequence of human PSA

<400> SEQUENCE: 7

Ala Pro Leu Ile Leu Ser Arg Ile Val Gly Gly Trp Glu Cys Glu Lys
1               5                   10                  15

His Ser Gln Pro Trp Gln Val Leu Val Ala Ser Arg Gly Arg Ala Val
                20                  25                  30

Cys Gly Gly Val Leu Val His Pro Gln Trp Val Leu Thr Ala Ala His
            35                  40                  45

Cys Ile Arg Asn Lys Ser Val Ile Leu Leu Gly Arg His Ser Leu Phe
```

```
                50                  55                  60
His Pro Glu Asp Thr Gly Gln Val Phe Gln Val Ser His Ser Phe Pro
 65                  70                  75                  80

His Pro Leu Tyr Asp Met Ser Leu Leu Lys Asn Arg Phe Leu Arg Pro
                     85                  90                  95

Gly Asp Asp Ser Ser His Asp Leu Met Leu Leu Arg Leu Ser Glu Pro
                100                 105                 110

Ala Glu Leu Thr Asp Ala Val Lys Val Met Asp Leu Pro Thr Gln Glu
            115                 120                 125

Pro Ala Leu Gly Thr Thr Cys Tyr Ala Ser Gly Trp Gly Ser Ile Glu
        130                 135                 140

Pro Glu Glu Phe Leu Thr Pro Lys Lys Leu Gln Cys Val Asp Leu His
145                 150                 155                 160

Val Ile Ser Asn Asp Val Cys Ala Gln Val His Pro Gln Lys Val Thr
                165                 170                 175

Lys Phe Met Leu Cys Ala Gly Arg Trp Thr Gly Gly Lys Ser Thr Cys
                180                 185                 190

Ser Gly Asp Ser Gly Gly Pro Leu Val Cys Asn Gly Val Leu Gln Gly
            195                 200                 205

Ile Thr Ser Trp Gly Ser Glu Pro Cys Ala Leu Pro Glu Arg Pro Ser
        210                 215                 220

Leu Tyr Thr Lys Val Val His Tyr Arg Lys Trp Ile Lys Asp Thr Ile
225                 230                 235                 240

Val Ala Asn Pro

<210> SEQ ID NO 8
<211> LENGTH: 119
<212> TYPE: PRT
<213> ORGANISM: Artificial Sequence
<220> FEATURE:
<223> OTHER INFORMATION: Heavy chain variable region amino acid sequence

<400> SEQUENCE: 8

Gln Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Thr
                20                  25                  30

Gly Met Gly Val Ser Trp Ile Arg Gln Pro Pro Gly Lys Ala Leu Glu
            35                  40                  45

Trp Leu Ala His Ile Tyr Trp Asp Asp Asp Lys Arg Tyr Ser Thr Ser
        50                  55                  60

Leu Lys Thr Arg Leu Thr Ile Ser Glu Asp Ser Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Lys Gly Tyr Tyr Gly Tyr Phe Asp Tyr Trp Gly Gln Gly
                100                 105                 110

Thr Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Light chain variable region amino acid sequence
```

<400> SEQUENCE: 9

Asp Ile Gln Met Thr Gln Ser Pro Ser Leu Ser Ala Ser Val Gly
1               5                   10                  15

Asp Arg Val Thr Val Thr Cys Arg Ala Ser Gln Asn Val Asn Thr Asp
            20                  25                  30

Val Ala Trp Tyr Gln Gln Lys Pro Gly Lys Ala Pro Lys Ala Leu Ile
        35                  40                  45

Phe Ser Thr Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Tyr Pro Leu
                85                  90                  95

Thr Phe Gly Gln Gly Thr Lys Val Glu Ile Lys
            100                 105

<210> SEQ ID NO 10
<211> LENGTH: 330
<212> TYPE: PRT
<213> ORGANISM: Artificial Sequence
<220> FEATURE:
<223> OTHER INFORMATION: Antibody amino acid sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr

```
                        245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 11
<211> LENGTH: 106
<212> TYPE: PRT
<213> ORGANISM: Artificial Sequence
<220> FEATURE:
<223> OTHER INFORMATION: Antibody amino acid sequence

<400> SEQUENCE: 11

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 12
<211> LENGTH: 449
<212> TYPE: PRT
<213> ORGANISM: Artificial Sequence
<220> FEATURE:
<223> OTHER INFORMATION: Heavy chain amino acid sequence

<400> SEQUENCE: 12

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Thr
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Ser Thr Ser
    50                  55                  60

Leu Lys Thr Arg Leu Thr Ile Ser Glu Asp Ser Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Gly Tyr Gly Tyr Phe Asp Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 214
<212> TYPE: PRT
<213> ORGANISM: Artificial Sequence
<220> FEATURE:
<223> OTHER INFORMATION: Light chain amino acid sequence

<400> SEQUENCE: 13

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Asn Val Asn Thr Asp
```

```
            20                  25                  30
Val Ala Trp Tyr Gln Gln Lys Pro Gly Lys Ala Pro Lys Ala Leu Ile
        35                  40                  45

Phe Ser Thr Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 357
<212> TYPE: DNA
<213> ORGANISM: Artificial Sequence
<220> FEATURE:
<221> NAME/KEY: source
<222> LOCATION: 1..357
<223> OTHER INFORMATION: /mol_type="unassigned DNA"
      /note="Nucleic acid sequence"
      /organism="Artificial Sequence"

<400> SEQUENCE: 14
caggtcacac tgaaggaatc tgggcctgct ttggtgaagc ccactcagac tctgacactc      60
acatgcacct tctccgggtt tagcctgtca accaccggta tgggcgtgag ttggattcgc     120
caaccaccgg gtaaagcgct tgagtggctt gcacacatct attgggacga tgacaagcgg     180
tacagtacta gcctgaaaac gagactgacc ataagcgagg actcatccaa gaatcaggtg     240
gtactgacga tgaccaacat ggatcccgtt gataccgcca catactactg tgccaggaaa     300
ggctactatg gctatttcga ctattgggga cagggaacac tcgtcactgt gtcctct        357

<210> SEQ ID NO 15
<211> LENGTH: 324
<212> TYPE: DNA
<213> ORGANISM: Artificial Sequence
<220> FEATURE:
<221> NAME/KEY: source
<222> LOCATION: 1..324
<223> OTHER INFORMATION: /mol_type="unassigned DNA"
      /note="Nucleic acid sequence"
      /organism="Artificial Sequence"

<400> SEQUENCE: 15
gacatccaga tgacccaatc tccctctagc ttgtccgcta gtgtcggtga tagggtgaca      60
```

```
gtgacatgca gagctagcca gaatgtcaac acagacgttg cctggtatca gcagaagcca     120
ggcaaagcac ccaaagccct catcttctcc acgtcatatc tgcaaagcgg agtaccttcc     180
cggtttagtg ggtctgggtc aggcactgac ttcaccctga ccatatccag ccttcaaccg     240
gaagatttcg cgacctacta ctgtcagcag tacagcaact atcctctgac ttttggacag     300
ggcactaagg tggagattaa gcgt                                             324
```

```
<210> SEQ ID NO 16
<211> LENGTH: 1350
<212> TYPE: DNA
<213> ORGANISM: Artificial Sequence
<220> FEATURE:
<221> NAME/KEY: source
<222> LOCATION: 1..1350
<223> OTHER INFORMATION: /mol_type="unassigned DNA"
      /note="Nucleic acid sequence"
      /organism="Artificial Sequence"

<400> SEQUENCE: 16
```

```
caggtcacac tgaaggaatc tgggcctgct ttggtgaagc ccactcagac tctgacactc     60
acatgcacct tctccgggtt tagcctgtca accaccggta tgggcgtgag ttggattcgc    120
caaccaccgg gtaaagcgct tgagtggctt gcacacatct attgggacga tgacaagcgg    180
tacagtacta gcctgaaaac gagactgacc ataagcgagg actcatccaa gaatcaggtg    240
gtactgacga tgaccaacat ggatcccgtt gataccgcca catactactg tgccaggaaa    300
ggctactatg gctatttcga ctattgggga cagggaacac tcgtcactgt gtcctctgct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                     1350
```

```
<210> SEQ ID NO 17
<211> LENGTH: 642
<212> TYPE: DNA
<213> ORGANISM: Artificial Sequence
<220> FEATURE:
<221> NAME/KEY: source
<222> LOCATION: 1..642
```

<223> OTHER INFORMATION: /mol_type="unassigned DNA"
      /note="Nucleic acid sequence"
      /organism="Artificial Sequence"

<400> SEQUENCE: 17
gacatccaga tgacccaatc tccctctagc ttgtccgcta gtgtcggtga tagggtgaca      60
gtgacatgca gagctagcca gaatgtcaac acagacgttg cctggtatca gcagaagcca     120
ggcaaagcac ccaaagccct catcttctcc acgtcatatc tgcaaagcgg agtaccttcc     180
cggtttagtg ggtctgggtc aggcactgac ttcaccctga ccatatccag ccttcaaccg     240
gaagatttcg cgacctacta ctgtcagcag tacagcaact atcctctgac ttttggacag     300
ggcactaagg tggagattaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg ataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 18
<211> LENGTH: 7
<212> TYPE: PRT
<213> ORGANISM: Artificial Sequence
<220> FEATURE:
<223> OTHER INFORMATION: N terminal amino acid sequence from light chain
      of antibody

<400> SEQUENCE: 18

Asp Ile Val Met Thr Gln Ser
1               5

<210> SEQ ID NO 19
<211> LENGTH: 8
<212> TYPE: PRT
<213> ORGANISM: Artificial Sequence
<220> FEATURE:
<223> OTHER INFORMATION: N terminal amino acid sequence from heavy chain
      of antibody

<400> SEQUENCE: 19

Glu Val Gln Leu Val Glu Ser Gly
1               5

<210> SEQ ID NO 20
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Light chain primer 5A10-L "
      /organism="Artificial Sequence"

<400> SEQUENCE: 20
ccagccatgg ctgacattgt gatgacccag tctca                                35

<210> SEQ ID NO 21
<211> LENGTH: 34
<212> TYPE: DNA
<213> ORGANISM: Artificial Sequence
<220> FEATURE:
<221> NAME/KEY: source

```
<222> LOCATION: 1..34
<223> OTHER INFORMATION: /mol_type="unassigned DNA"
      /note="Light chain primer WO252"
      /organism="Artificial Sequence"

<400> SEQUENCE: 21
gcgccgtcta gaattaacac tcattcctgt tgaa                              34

<210> SEQ ID NO 22
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Fd chain primer 5A10-H "
      /organism="Artificial Sequence"

<400> SEQUENCE: 22
ccagccatgg ctgaggtgca attggtggag tctgg                             35

<210> SEQ ID NO 23
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Fd chain primer WO267"
      /organism="Artificial Sequence"

<400> SEQUENCE: 23
ctagactagt acaatccctg ggcacaattt tc                                32

<210> SEQ ID NO 24
<211> LENGTH: 237
<212> TYPE: PRT
<213> ORGANISM: Homo Sapiens

<400> SEQUENCE: 24
```

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
                20                  25                  30

Pro Gln Trp Val Leu Thr Ala Ala His Cys Ile Arg Asn Lys Ser Val
            35                  40                  45

Ile Leu Leu Gly Arg His Ser Leu Phe His Pro Glu Asp Thr Gly Gln
        50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

-continued

```
Ala Gln Val His Pro Gln Lys Val Thr Lys Phe Met Leu Cys Ala Gly
            165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
            195                 200                 205

Pro Cys Ala Leu Pro Glu Arg Pro Ser Leu Tyr Thr Lys Val Val His
            210                 215                 220

Tyr Arg Lys Trp Ile Lys Asp Thr Ile Val Ala Asn Pro
225                 230                 235
```

US 11,332,543 B2

ANTIBODY POLYPEPTIDES AND USES THEREOF

This application is a § 371 application of PCT/EP2016/073684, filed Oct. 4, 2016, which in turn claims priority to GB Application 1517550.8, filed Oct. 5, 2015, and GB Application 1519105.9, filed Oct. 29, 2015. The entire disclosure of each of the foregoing applications is incorporated by reference herein.

FIELD OF THE INVENTION

This invention pertains in general to the field of therapeutic and diagnostic agents and methods, particularly in field of prostate cancer.

BACKGROUND

Prostate cancer is at the present time the most common form of cancer among men. The prostate is a walnut-sized gland in men that produces fluid that is a component in semen. The prostate has two or more lobes, or sections, enclosed by an outer layer of tissue. The prostate is located in front of the rectum and just below the urine bladder, and surrounds the urethra.

The occurrence of prostate cancer is highest in the northwestern part of Europe and in the United States. The growth of the tumour is usually a process that takes place during a long period of time. Prostate cancer is normally a mild form of cancer. In fact, the majority of men diagnosed with prostate cancer survive and recover, with only a minority of the men encountering a more aggressive form of prostate cancer, which metastasizes in an early stage. This aggressive form of prostate cancer may only be curable if it is diagnosed at an early stage, before the cancer has spread to extracapsular tissue.

Today, diagnosis and monitoring of prostate cancer is typically performed by measuring the concentration of a prostate specific antigen (PSA) in the blood of the patient. If the concentration of PSA is markedly high in several consecutive measurements, performed at different points of time, the assessment is that there is a probability of prostate cancer. At this point of time a biopsy may be performed to verify prostate cancer.

PSA (also known as kallikrein III) is a protein, constituted of a single chain of 237 amino acids, which is produced in the secretory cells of the prostate. These secretory cells may be found in the whole prostate gland. PSA is well established and thoroughly researched marker in respect of prostate cancer. By comparison with healthy cells the production of PSA is lower in malignant cells and higher in hyperplastic cells. It is rather contradictory that in fact the concentration of PSA is higher in blood from men suffering from prostate cancer. However, one explanation may be that the malignant cells have a deteriorated cell structure, and are therefore more permeable to PSA.

Another important serine protease suitable as a target for therapy of prostate cancer is human glandular kallikrein 2 (hK2). The gene coding hK2 is located on chromosome 19, together with the gene coding for PSA. hK2 is expressed mainly in the prostate tissue, just as PSA. In the prostate, PSA is present as an inactive pro-form and is activated through the peptidase action of hK2. Immunohistochemical research in respect of hK2 has shown that hK2 is expressed in relation to the level of differentiation. This means that hK2 is expressed in a higher yield in tissue of low differentiation, such as tissue subjected to prostate cancer, and in a lower yield in tissue of high differentiation, such as tissue subjected to benign prostatic hyperplasia (BPH) which is another common prostate problem.

Today's therapies of prostate cancer are surgery (e.g., radical prostatectomy), radiation therapy (including, radium-223 chloride administration, brachytherapy and external beam radiation therapy), high-intensity focused ultrasound (HIFU), chemotherapy, oral chemotherapeutic drugs, cryosurgery (freezing the tumor), hormonal therapy (such as antiandrogen therapy), castration or combinations of the foregoing.

Most of these therapies (surgery and external radiation therapy) are, however, only (or primarily) useful for treatment of primary tumours and large metastases. Chemotherapy is used for disseminated of the cancer but for most of these patients, it is a palliative effect and/or prolonged survival. Other or complementary treatment modalities are therefore necessary to achieve considerable improvements of the disseminated malignant diseases, particular in cases of micrometastases.

Therapy, such as immunotherapy or radioimmunotherapy, using targeting molecules such as antibodies and fragments thereof could give the possibility of therapy of disseminated disease.

Thus, there is a need for a new therapeutic agents and methods for treating and diagnosing prostate cancer.

SUMMARY OF THE INVENTION

Accordingly, the present invention seeks to mitigate, alleviate or eliminate one or more of the above-identified deficiencies in the art and disadvantages singly or in any combination and solves at least the above mentioned problems by providing a therapeutic agents and methods according to the appended patent claims.

A first aspect of the present invention provides an antibody polypeptide with binding specificity for prostate specific antigen (PSA), wherein the antibody polypeptide comprises
(a) a heavy chain variable region comprising the amino acid sequences of SEQ ID NO:1 and SEQ ID NO:2 and SEQ ID NO:3

| CDRH1: | TTGMGVS | SEQ ID NO: 1 |
| CDRH2: | HIYWDDDKRYSTSLK | SEQ ID NO: 2 |
| CDRH3: | KGYYGYFDY | SEQ ID NO: 3 | and/or
(b) a light chain variable region comprising the amino acid sequences of SEQ ID NO:4 and SEQ ID NO:5 and SEQ ID NO:6

| CDRL1: | RASQNVNTDVA | SEQ ID NO: 4 |
| CDRL2: | STSYLQS | SEQ ID NO: 5 |
| CDRL3: | QQYSNYPLT | SEQ ID NO: 6 | and wherein the heavy chain variable region and light chain variable region comprise framework amino acid sequences from one or more human antibodies.

The above six amino acid sequences represent the complementarity-determining regions (CDRs) of the antibody polypeptides of the invention, as defined according to Kabat et al., (1991) *Sequences of Immunological Interest*, 5th edition, NIH, Bethesda, Md. (the disclosures of which are incorporated herein by reference).

By "antibody polypeptide" we include substantially intact antibody molecules, single chain antibodies, diabodies, bispecific antibodies, antibody heavy chains, antibody light chains, homodimers and heterodimers of antibody heavy and/or light chains, as well as antigen binding fragments and derivatives of the same.

The term "amino acid" as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides as defined herein comprise or consist of L-amino acids.

The antibody polypeptides of the invention exhibit specificity for PSA, and preferably the mature, active form of human PSA.

The amino acid sequence of human PSA is shown below

[SEQ ID NO: 7]
APLILS<u>RIVGGWECEKHSQPWQVLVASRGRAVCGGVLVHPQWVLTAAHCI</u>

<u>RNKSVILLGRHSLFHPEDTGQVFQVSHSFPHPLYDMSLLKNRFLRPGDDS</u>

<u>SHDLMLLRLSEPAELTDAVKVMDLPTQEPALGTTCYASGWGSIEPEEFLT</u>

<u>PKKLQCVDLHVISNDVCAQVHPQKVTKFMLCAGRWTGGKSTCSGDSGGPL</u>

<u>VCNGVLQGITSWGSEPCALPERPSLYTKVVHYRKWIKDTIVANP</u>

(wherein the sequence of the mature, active PSA protein is underlined (SEQ ID NO: 24); see also UniProtKB Accession NO. P07288).

Most of the PSA found in seminal plasma is inactive and complexed with protein C inhibitor (PCI). It is also possible that PSA forms complexes with other extracellular protease inhibitors. In vitro studies show that PSA may bind to α2-antiplasmin (α2-AP), ACT, AMG, anti-thrombin III (ATM), C1-inactivator and plasminogen activator inhibitor-1 (PAI-1).

In one embodiment, the antibody polypeptide has specificity for the free (that is, non-complexed) isoform of PSA compared to the complexed isoform of PSA. Binding moieties with specificity for the free isoform of PSA may have binding specificity for an epitope that is exposed on the free isoform of PSA, but is unexposed on the complexed isoform of PSA, and this may be a linear or a conformational (that is, non-linear) epitope. For example, the antibody polypeptide may have specificity for an epitope that includes one or more amino acid residues that are part of the catalytic cleft of PSA that is exposed in free PSA and unexposed in a complexed isoform, such as the form present in seminal fluid when PSA is complexed to PCI.

By "specificity" we mean that the antibody polypeptide is capable of binding to PSA in vivo, i.e. under the physiological conditions in which PSA exists within the human body. Preferably, the antibody polypeptide does not bind to any other protein in vivo.

Such binding specificity may be determined by methods well known in the art, such as ELISA, immunohistochemistry, immunoprecipitation, Western blots and flow cytometry using transfected cells expressing PSA. Advantageously, the antibody polypeptide is capable of binding selectively to PSA, i.e. it binds at least 10-fold more strongly to PSA than to another proteins (in particular, other kallikreins such as prostate specific antigen or PSA).

The antibody polypeptides of the present invention are based on a selected humanised version of the 5A10 antibody, which exhibits unexpected favourable properties.

In particular, the humanised antibodies of the invention exhibit an enhanced uptake into tumours compared to the parent murine 5A10 antibody (m5A10) from which their CDR sequences were derived (see Example 6).

By "enhanced uptake into tumours" we mean that the antibody polypeptide of the invention (a humanised form of the 5A10 antibody), when administered to a patient with a prostate tumour can provide a higher tumour absorbed dose than the parent murine 5A10 antibody with less normal organ toxicity.

The unexpectedly better tumor accumulation provides a better therapeutic profile of the antibodies of the invention. It in turn permit higher radiation doses (absorbed doses) to be used, leading to greater efficacy in the treatment of prostate cancer without increasing side-effects or 'collateral damage' to healthy tissues and organs.

Humanisation (also called reshaping or CDR-grafting) is a technique for reducing the immunogenicity of monoclonal antibodies from xenogeneic sources (commonly, from rodents such as mice) and for improving their activation of the human immune system (see review by Almagro & Fransson, 2008, *Frontiers in Bioscience* 13:1619-1633; the disclosures of which are incorporated herein by reference). There are several humanised monoclonal antibodies in clinical trials and a few have been given approval to be used as drugs. Although the mechanics of producing the engineered monoclonal antibody using the techniques of molecular biology are relatively straightforward, simple grafting of the rodent complementarity-determining regions (CDRs) into human frameworks does not always reconstitute the binding affinity and specificity of the original monoclonal antibody. In order to humanize an antibody, the design of the humanised antibody is a critical step in reproducing the function of the original molecule.

The design of a humanised antibody includes several key choices, including the extents of the CDRs to be used and the human frameworks to be used. However, in order to retain the specificity of the parent antibody, it may also be critical to substitute one or more residues from the rodent mAb into the human framework regions (so-called backmutations). Identifying the position of the necessary backmutations requires a detailed sequence/structural analysis. Recently, phage libraries have been used to vary the amino acids at chosen positions. Similarly, many approaches have been used to choose the most appropriate human frameworks in which to graft the rodent CDRs. Early experiments used a limited subset of well-characterised human monoclonal antibodies (often where the structure was available), irrespective of the sequence identity to the rodent monoclonal antibody (the so-called fixed frameworks approach). Some groups use variable regions with high amino acid sequence identity to the rodent variable regions (homology matching or best-fit); others use consensus or germline sequences while still others select fragments of the framework sequences within each light or heavy chain variable region from several different human monoclonal antibodies. There are also approaches to humanisation developed which replace the surface rodent residues with the most common residues found in human monoclonal antibodies ("resurfacing" or "veneering") and those which use differing definitions of the extents of the CDRs.

However, despite extensive study of antibody humanisation, some rodent monoclonal antibodies have proved difficult to humanise.

Development of the antibody polypeptides of the invention required backmutations not only in the framework regions but also in some of the CDRs (see Example 2 below). Thus, the six CDR sequences represented above in SEQ ID NOS: 1 to 6 are derived from the murine anti-PSA antibody 5A10, but contain mutations in CDRH2 (SEQ ID NO: 2) and CDRL1 (SEQ ID NO: 4) relative to the parent murine antibody. These mutations in the CDRs were made in order to confer optimal specificity and stability on the humanised version of 5A10.

In one embodiment, the antibody polypeptides of the invention bind PSA with a $K_D$ of greater than $0.1 \times 10^{-9}$ M.

Methods for measuring the overall affinity ($K_D$) and on-rate (ka) and off-rate (kd) of an interaction (such as an interaction between an antibody and a ligand) are well known in the art. Exemplary in vitro methods are described in Example 3 below. It is also conceivable to use flow cytometry based methods (Sklar et al., 2002, *Annu Rev Biophys Biomol Struct*, 31:97-119; the disclosures of which are incorporated herein by reference).

Advantageously, the antibody polypeptide of the invention has an affinity ($K_D$) for PSA of lower than $1.0 \times 10^{-10}$ M, for example a $K_D$ lower than $9.0 \times 10^{-11}$ M, $8.0 \times 10^{-11}$ M, $7.0 \times 10^{-11}$ M, $6.0 \times 10^{-11}$ M, $5.0 \times 10^{-11}$ M, $4.0 \times 10^{-11}$ M, $3.0 \times 10^{-11}$ M, $2.0 \times 10^{-11}$ M or lower than $1.0 \times 10^{-11}$ M.

It will be appreciated by persons skilled in the art that the antibody polypeptides of the invention may constitute antibody heavy chains, antibody light chains, homodimers and heterodimers of antibody heavy and/or light chains, and antigen binding fragments and derivatives of the same.

In one embodiment, the antibody polypeptide comprises or consists of an intact (i.e. complete) antibody, such as an IgA, IgD, IgE, IgG or IgM molecule.

Advantageously, the antibody polypeptide comprises or consists of an intact IgG molecule, or an antigen-binding fragment or derivative of the same.

The IgG molecule may be of any known subtype, for example IgG1, IgG2, IgG3 or IgG4.

By "antigen-binding fragments and derivatives" of antibodies we include Fv fragments (e.g. single chain Fv and disulphide-bonded Fv), Fab-like fragments (e.g. Fab fragments, Fab' fragments and F(ab)$_2$ fragments) and domain antibodies (e.g. single $V_H$ variable domains or $V_L$ variable domains).

For example, the antibody polypeptide may comprise or consist of an scFv or Fab fragment.

A further characterising feature of the antibody polypeptides of the present invention is the presence of framework amino acid sequences from one or more human antibodies in the heavy and light chain variable regions.

By "framework sequences" we include the regions of the heavy and light chain variable domains other than the CDRs. Typically, each variable domain will comprise four framework regions, designated FR1 to FR4, within which the CDR sequences are located:

FR1----CDR1----FR2----CDR2----FR3----CDR3----FR4

It will be appreciated that the amino acid sequences of the framework regions may be fully human or may contain one or more backmutations (i.e. the amino acid sequence present in the human framework may be substituted with the amino acid found at the corresponding position within the parent rodent variable domain from which the CDRs are derived). Consequently, the sequences of FR1, FR2, FR3 and/or FR4 of the heavy and/or light chain variable domain(s) of the antibody polypeptide of the invention may be non-naturally occurring.

In one embodiment, the framework sequences of the antibody polypeptide share at least 70% sequence identity with framework regions from one or more human antibodies, for example at least 80%, 85%, 90%, 95%, 96%, 97%, 98%, 99% or more. Thus, the antibody polypeptide may comprise a heavy chain FR1 region that shares least 70% sequence identity with an FR1 region of a human antibody. It will be appreciated, however, that the heavy and light chains of the antibody polypeptide may share sequence identity with the framework regions of different human antibodies.

Percent identity can be determined by, for example, the LALIGN program (Huang and Miller, Adv. Appl. Math. (1991) 12:337-357) at the Expasy facility site (http://www.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (as described in Thompson et al., 1994, *Nucl. Acid Res.* 22:4673-4680, which is incorporated herein by reference). The parameters used may be as follows:

Fast pair-wise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

In one embodiment, the framework sequences of the heavy variable domain of the antibody polypeptide of the invention are encoded by the human immunoglobulin VH4 gene family.

For example, the framework sequences may be encoded, at least in part, by a VH4-28 germline gene (e.g. FR1, FR2 and FR3 may be encoded by VH4-28 and FR4 may be encoded by JH1).

Thus, in one embodiment, the antibody polypeptide may comprise or consist of a heavy chain variable region which comprises or consists of the amino acid sequence of SEQ ID NO:8 (wherein the CDR sequences are underlined in bold):

[SEQ ID NO: 8]
Q V T L K E S G P A L V K P T Q T L T L T C T F S

G F S L S T T G M G V S W I R Q P P G K A L E W L

A H I Y W D D D K R Y S T S L K T R L T I S E D S

-continued
S K N Q V V L T M T N M D P V D T A T Y Y C A R K

G Y Y G Y F D Y W G Q G T L V T V S S

In one embodiment, the framework sequences of the light variable domain of the antibody polypeptide of the invention are encoded by the human immunoglobulin Kappa V4 gene family.

For example, the framework sequences may be encoded, at least in part, by an IgkV4-B3 germline gene (e.g. FR1, FR2 and FR3 may be encoded by IgkV4-B3 and FR4 may be encoded by JK2).

Thus, in one embodiment, the antibody polypeptide may comprise or consist of a light chain variable region which comprises or consists of the amino acid sequence of SEQ ID NO: 9 (wherein the CDR sequences are underlined in bold):

[SEQ ID NO: 9]
D I Q M T Q S P S S L S A S V G D R V T V T C R A

S Q N V N T D V A W Y Q Q K P G K A P K A L I F S

T S Y L Q S G V P S R F S G S G S G T D F T L T I

S S L Q P E D F A T Y Y C Q Q Y S N Y P L T F G Q

G T K V E I K

By "at least in part" we include that the framework sequences comprise at least ten contiguous amino acids encoded by the reference gene, for example at least 20 contiguous amino acids. We also include that one or more, but not all, the FR regions are encoded by the reference gene (for example, FR1 and FR2 may be encoded by the reference gene, but not FR3).

In a preferred embodiment, the antibody polypeptide comprises a heavy chain variable region which comprises or consists of the amino acid sequence of SEQ ID NO:8 and a light chain variable region which comprises or consists of the amino acid sequence of SEQ ID NO: 9.

Optionally, the antibody polypeptide of the invention further comprises a heavy chain constant region, or part thereof.

In one embodiment, the antibody polypeptide comprises a CH1, CH2 and/or CH3 region of an IgG heavy chain (such as an IgG1, IgG2, IgG3 or IgG4 heavy chain). Thus, the antibody polypeptide may comprise part or all of the constant regions from an IgG1 heavy chain. For example, the antibody polypeptide may be a Fab fragment comprising CH1 and CL constant regions.

In one embodiment, the antibody polypeptide may comprise an antibody Fc-region. It will be appreciated by a skilled person that the Fc portion may be from an IgG antibody, or from a different class of antibody (such as IgM, IgA, IgD or IgE). In one embodiment, the Fc region is from an IgG1, IgG2, IgG3 or IgG4 antibody.

The Fc region may be naturally-occurring (e.g. part of an endogenously produced antibody) or may be artificial (e.g. comprising one or more point mutations relative to a naturally-occurring Fc region and/or modifications to the carbohydrate moieties within the CH2 domain). Fc-regions with point mutations improving their ability to bind FcR may be advantageous, e.g. by altering serum half-life or by modulating (i.e. enhancing or reducing) binding to Fcγ receptors (FcγR) involved in ADCC and CDC.

Advantageously, the antibody polypeptide may comprise the amino acid sequence of SEQ ID NO: 10, or part thereof:

[SEQ ID NO: 10]
A S T K G P S V F P L A P S S K S T S G G T A A L

G C L V K D Y F P E P V T V S W N S G A L T S G V

H T F P A V L Q S S G L Y S L S S V V T V P S S S

L G T Q T Y I C N V N H K P S N T K V D K K V E P

K S C D K T H T C P P C P A P E L L G G P S V F L

F P P K P K D I L M I S R T P E V T C V V V D V S

H E D P E V K F N W Y V D G V E V H N A K T K P R

E E Q Y N S T Y R V V S V L T V L H Q D W L N G K

E Y K C K V S N K A L P A P I E K T I S K A K G Q

P R E P Q V Y T L P P S R E E M T K N Q V S L T C

L V K G F Y P S D I A V E W E S N G Q P E N N Y K

T T P P V L D S D G S F F L Y S K L T V D K S R W

Q Q G N V F S C S V M H E A L H N H Y T Q K S L S

L S P G K

Optionally, the antibody polypeptide of the invention further comprises a light chain constant region, or part thereof.

In one embodiment, the antibody polypeptide comprises a CL region of an IgG light chain (such as a kappa or lambda light chain)

For example, the antibody polypeptide may comprise the amino acid sequence of SEQ ID NO: 11, or part thereof:

[SEQ ID NO: 11]
T V A A P S V F I F P P S D E Q L K S G T A S V V

C L L N N F Y P R E A K V Q W K V D N A L Q S G N

S Q E S V T E Q D S K D S T Y S L S S T L T L S K

A D Y E K H K V Y A C E V T H Q G L S S P V T K S

F N R G E C

Advantageously, the antibody polypeptide comprises a heavy chain constant region which comprises or consists of the amino acid sequence of SEQ ID NO: 10 and a light chain constant region which comprises or consists of the amino acid sequence of SEQ ID NO: 11.

In one preferred embodiment, the antibody polypeptide of the invention comprises:
(a) a heavy chain which comprises or consists of the amino acid sequence of SEQ ID NO: 12 (wherein the variable region is in bold and the CDR sequences are underlined)

[SEQ ID NO: 12]
Q V T L K E S G P A L V K P T Q T L T L T C T F S

G F S L S <u>T T G M G V S</u> W I R Q P P G K A L E W L

A <u>H I Y W D D D K R Y S T S L K</u> T R L T I S E D S

S K N Q V V L T M T N M D P V D T A T Y Y C A R <u>K</u>

<u>G Y Y G Y F D Y</u> W G Q G T L V T V S S A S T K G P

S V F P L A P S S K S T S G G T A A L G C L V K D

Y F P E P V T V S W N S G A L T S G V H T F P A V

-continued

LQSSGLYSLSSVVTVPSSSLGTQTY

ICNVNHKPSNTKVDKKVEPKSCDKT

HTCPPCPAPELLGGPSVFLFPPKPK

DILMISRTPEVTCVVVDVSHEDPEV

KFNWYVDGVEVHNAKTKPREEQYNS

TYRVVSVLTVLHQDWLNGKEYKCKV

SNKALPAPIEKTISKAKGQPREPQV

YTLPPSREEMTKNQVSLTCLVKGFY

PSDIAVEWESNGQPENNYKTTPPVL

DSDGSFFLYSKLTVDKSRWQQGNVF

SCSVMHEALHNHYTQKSLSLSPGK and/or (b) a light chain which comprises or consists of the amino acid sequence of SEQ ID NO: 13 (wherein the variable region is in bold and the CDR sequences are underlined)

[SEQ ID NO: 13]

DIQMTQSPSSLSASVGDRVTVTCRA

SQNVNTDVAWYQQKPGKAPKALIFS

TSYLQSGVPSRFSGSGSGTDFTLTI

SSLQPEDFATYYCQQYSNYPLTFGQ

GTKVEIKRTVAAPSVFIFPPSDEQL

KSGTASVVCLLNNFYPREAKVQWKV

DNALQSGNSQESVTEQDSKDSTYSL

SSTLTLSKADYEKHKVYACEVTHQG

LSSPVTKSFNRGEC

For example, the antibody polypeptide may comprise or consist of two heavy chains of SEQ ID NO: 12 and two light chains of SEQ ID NO: 13, joined together by disulphide bridges to form a typical IgG antibody structure.

The antibody polypeptides of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

It will be appreciated by persons skilled in the art that the antibody polypeptides of the invention may be augmented with a functional moiety to facilitate their intended use, for example as an in vivo imaging agent or therapeutic agent.

Thus, in one embodiment, the antibody polypeptide is linked, directly or indirectly, to a therapeutic moiety.

Any suitable therapeutic moiety may be used. A suitable therapeutic moiety is one that is capable of reducing or inhibiting the growth, or in particular killing, a prostatic cancer cell. For example, the therapeutic agent may be a cytotoxic moiety. A cytotoxic moiety may comprise or consist of one or more radioisotopes. For example, the one or more radioisotopes may each be independently selected from the group consisting of beta-emitters, Auger-emitters, conversion electron-emitters, alpha-emitters, and low photon energy-emitters. It may be desired that the one or more radioisotopes each independently has an emission pattern of locally absorbed energy that creates a high absorbed dose in the vicinity of the agent. Exemplary radioisotopes may include long-range beta-emitters, such as $^{90}$Y, $^{32}$P, $^{186}$Re/$^{188}$Re; $^{166}$Ho, $^{76}$As/$^{77}$As, $^{89}$Sr, $^{153}$Sm; medium range beta-emitters, such as $^{131}$I, $^{177}$Lu, $^{67}$Cu, $^{161}$Tb, $^{105}$Rh, low-energy beta-emitters, such as $^{45}$Ca or $^{35}$S; conversion or Auger-emitters, such as $^{51}$Cr, $^{67}$Ga, $^{99}$Tc$^m$, $^{111}$In, $^{114m}$In, $^{123}$I, $^{125}$I, $^{201}$Tl; and alpha-emitters, such as $^{212}$Bi, $^{213}$Bi, $^{223}$Ac, $^{225}$Ac, $^{212}$Pb, $^{255}$Fm, $^{223}$Ra, $^{149}$Tb and $^{221}$At. Other radionuclides are available and will be possible to use for therapy.

In another embodiment, it may be desired that the therapeutic moiety or cytotoxic moiety is not a moiety as disclosed as a "tracer" in WO 2006/087374 A1, in particular at page 11, lines 7-15 thereof.

In one preferred embodiment, the antibody polypeptide is linked to (or otherwise labelled with) the radioisotope $^{177}$Lu.

Alternatively, the therapeutic moiety may comprise or consist of one or more therapeutic (such as cytotoxic) drugs, for example, a cytostatic drug; an anti-androgen drug; cortisone and derivatives thereof; a phosphonate; a testosterone-5-α-reductase inhibitor; a boron addend; a cytokine; thapsigargin and its metabolites; a toxin (such as saporin or calicheamicin); a chemotherapeutic agent (such as an antimetabolite); or any other therapeutic or cytotoxic drug useful in the treatment of prostatic carcinoma.

Exemplary therapeutic/cytotoxic drugs may, for example, include:

Cytostatics, in particular those with dose-limiting side-effects, including but not limited to cyclophosamide, chlorambucil, ifosfamide, busulphane, lomustine, taxanes, estramustine phosphate and other nitrogen mustards, antibiotics (including doxorubicine, calicheamicines and esperamicine), vinca alkaloids, azaridines, platinum-containing compounds, endostatin, alkyl sulfonates, nitrosoureas, triazenes, folic acid analoges, pyrimidine analoges, purine analogs, enzymes, substituted urea, methyl-hydrazine derivatives, daunorubicin, amphipathic amines, Anti-androgens such as flutamide and bikalutamide and metabolites thereof;

Cortisone and derivatives thereof;

Phosphonates such as diphophonate and buphosphonate;

Testosterone-5-α-reductase inhibitors;

Boron addends;

Cytokines;

Thapsigargin and its metabolites;

Other agents used in the treatment of prostatic carcinoma.

Alternatively, the cytotoxic moiety may comprise or consist of one or more moieties suitable for use in activation therapy, such as photon activation therapy, neutron activation therapy, neutron induced Auger electron therapy, synchrotron irradiation therapy or low energy X-ray photon activation therapy.

For example, with the antibody polypeptides of the invention there will be the potential of using synchrotron radiation (or low energy X-rays) for the advancement of radiotherapy, primarily focusing on so called photo-activation radiotherapy (PAT), in which the local energy deposition from external X-ray irradiation is enhanced in the cancer tissue by the interaction with a pre-administered, high-Z tumor-targeting agent.

The PAT treatment modality utilises monochromatic X-rays from a synchrotron source, such as provided by the ID17 biomedical beamline at the European Synchrotron Radiation Facility (ESRF) in Grenoble, and as anticipated to be available at other facilities in the future such as the new Swedish synchrotron facility, Max-IV.

As a further potential treatment modality, research on "induced Auger electron tumour therapy" is the coming European Spallation Source (ESS) in Lund, and hopefully a medical experimental station. Reactor-produced thermal and semi-thermal neutrons have for long been used for Boron-Neutron-Capture-Therapy, BNCT, both for pre-clinical experiments and for treatment of brain tumours with the induced alpha-particles and the recoil nucleus ($^7$Li) that gives a high locally absorbed energy (absorbed dose). A similar approach is to use neutrons and suitable tumour-targeting molecules labelled with stable nuclei with high cross-section for neutrons. Antibodies or peptides can for instance be labelled with stable Gadolinium ($^{157}$Gd) and act as the target molecule for the neutrons that are captured by the Gd-nucleus, so called Gadolinium Neutron Capture Therapy (GdNCT). By Monte Carlo techniques, the dose distribution in the tumour and the surrounding tissues is calculated as it results from γ-photons, neutrons, nuclear recoils, as well as characteristic x-rays, internal conversion and Auger-electrons from gadolinium or other potential elements.

As discussed above, the therapeutic moiety (such as a radioisotope, cytotoxic moiety or the like) may be linked directly, or indirectly, to the binding moiety (such as an antibody or fragment thereof). Suitable linkers are known in the art and include, for example, prosthetic groups, non-phenolic linkers (derivatives of N-succinimidyl-benzoates; dodecaborate), chelating moieties of both macrocyclics and acyclic chelators, such as derivatives of 1,4,7,10-tetraaza-cyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), derivatives of 3,6,9,15-Tetraazabicyclo[9.3.1]-pentadeca-1(15),11,13-triene-4-(S)-(4-isothiocyanato-benzyl)-3,6,9-triacetic acid (PCTA), derivatives of 5-S-(4-Aminobenzyl)-1-oxa-4,7,10-triazacyclododecane-4,7,10-tris(acetic acid) (DO3A) and other chelating moieties. The use of such linkers may be particularly appropriate in circumstances wherein the agent comprises or consists of an antibody or fragment thereof as the binding moiety linked, via a linker, to a radioisotope as the therapeutic moiety.

One preferred linker is DTPA, for example as used in $^{177}$Lu-DTPA-[antibody polypeptide of the invention].

A further preferred linker is deferoxamine, DFO, for example as used in $^{89}$Zr-DFO-[antibody polypeptide of the invention], preferably for diagnostic use.

Optionally, the antibody polypeptide of the invention may (or may not) further comprises a detectable moiety. For example, a detectable moiety may comprise or consist of a radioisotope, such as a radioisotope selected from the group consisting of $^{99m}$Tc, $^{111}$In, $^{67}$Ga, $^{68}$Ga, $^{72}$As, $^{89}$Zr, $^{123}$I and $^{201}$Tl Optionally, the agent may comprise a pair of detectable and cytotoxic radionuclides, such as $^{86}$Y/$^{90}$Y or $^{124}$I/$^{211}$At. Alternatively, the agent may comprise a radioisotope that is capable of simultaneously acting in a multi-modal manner as a detectable moiety and also as a cytotoxic moiety to provide so-called "Multimodality theragnostics". The binding moieties may thus be coupled to nanoparticles that have the capability of multi-imaging (for example, SPECT, PET, MRI, Optical, or Ultrasound) together with therapeutic capability using cytotoxic drugs, such as radionuclides or chemotherapy agents. Also included with the present invention is the possibility of treatment by hyperthermia using high frequency alternating magnetic fields and accompanied ultrasound imaging.

Alternatively, the detectable moiety may comprise or consist of a paramagnetic isotope, such as a paramagnetic isotope is selected from the group consisting of $^{157}$Gd, $^{55}$Mn, $^{162}$Dy, $^{52}$Cr and $^{56}$Fe.

In the case that the antibody polypeptide comprises a detectable moiety, then the detectable moiety may be detectable by an imaging technique such as SPECT, PET, MRI, optical or ultrasound imaging.

Therapeutic and detectable moieties may be conjugated or otherwise combined with the antibody polypeptide using methods well known in the art (for example, the existing immunoconjugate therapy, gemtuzumab ozogamicin [tradename: Mylotarg®], comprises a monoclonal antibody linked to the cytotoxin calicheamicin).

In a further embodiment, the antibody polypeptide of the invention is used to treat prostate cancer in the form of a formulation comprising a population of antibody polypeptide molecules. In one option, all (or substantially all, such as greater than 90%, 95%, 99%, 99.9% or more, by weight) of the antibody polypeptide molecules in the population comprise the same therapeutic moiety. In another option, the population comprises a mixture of other agents with different therapeutic moieties. This option will give possibilities to enhance the effects of targeted radionuclide therapy using various agents such chemotherapy agents, hormonal therapy agents or other combination of therapies in which the targeting agent not only delivers therapeutically active radionuclides to tumor associated antigens but also simultaneously radiosensitizes the targeted tumor cells by modulating (e.g. triggering or blocking) an intracellular signaling cascade. This option is also useful in treating the prostate cancer with a mixture of cytotoxic agents, for example, using a cocktail of alpha- and different ranges of beta-emitters, or a cocktail of radionuclides with different range, LET (linear energy transfer) and RBE (relative biological effect), for combined treatment of large tumors, micrometastases, and single tumor cells. In one embodiment, long-range emitters may be used for treatment of large tumors, and short-range emitters may be used for the treatment of smaller tumours such as micrometastases, and single tumor cells.

Optionally, the antibody polypeptide of the present invention may (or may not) further comprises a moiety for increasing the in vivo half-life of the agent. Exemplary moieties for increasing the in vivo half-life of the agent may include polyethylene glycol (PEG), human serum albumin, glycosylation groups, fatty acids and dextran. PEG may be particularly contemplated.

It will be appreciated that the polypeptides of the invention may be lyophilised for storage and reconstituted in a suitable carrier prior to use, e.g. through freeze drying, spray drying, spray cooling, or through use of particle formation (precipitation) from supercritical carbon dioxide. Any suitable lyophilisation method (e.g. freeze-drying, spray drying, cake drying) and/or reconstitution techniques can be employed. It will be appreciated by those skilled in the art that lyophilisation and reconstitution can lead to varying degrees of activity loss and that use levels may have to be adjusted upward to compensate. Preferably, the lyophilised (freeze dried) polypeptide loses no more than about 1% of its activity (prior to lyophilisation) when rehydrated, or no more than about 5%, 10%, 20%, 25%, 30%, 35%, 40%, 45%, or no more than about 50% of its activity (prior to lyophilisation) when rehydrated.

Methods for the production of polypeptides of the invention are well known in the art.

Conveniently, the polypeptide is or comprises a recombinant polypeptide. Suitable methods for the production of such recombinant polypeptides are well known in the art, such as expression in prokaryotic or eukaryotic hosts cells (for example, see Sambrook & Russell, 2000, *Molecular Cloning, A Laboratory Manual*, Third Edition, Cold Spring Harbor, N.Y., the relevant disclosures in which document are hereby incorporated by reference).

Antibody polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that polypeptides of the invention may alternatively be synthesised artificially, for example using well known liquid-phase or solid phase synthesis techniques (such as t-Boc or Fmoc solid-phase peptide synthesis).

A second aspect of the invention provides an isolated nucleic acid molecule encoding an antibody polypeptide of the invention, or a component polypeptide chain thereof. By "nucleic acid molecule" we include DNA (e.g. genomic DNA or complementary DNA) and mRNA molecules, which may be single- or double-stranded.

In one embodiment, the nucleic acid molecule is a cDNA molecule.

It will be appreciated by persons skilled in the art that the nucleic acid molecule may be codon-optimised for expression of the antibody polypeptide in a particular host cell, e.g. for expression in human cells (for example, see Angov, 2011, *Biotechnol. J.* 6(6):650-659).

In a preferred embodiment, the nucleic acid molecule of the invention comprises
(a) the nucleotide sequence of SEQ ID NO: 14

```
                                            [SEQ ID NO: 14]
CAGGTCACACTGAAGGAATCTGGGCCTGCTTTGGTGAAGCCCACTCAGAC

TCTGACACTCACATGCACCTTCTCCGGGTTTAGCCTGTCAACCACCGGTA

TGGGCGTGAGTTGGATTCGCCAACCACCGGGTAAAGCGCTTGAGTGGCTT

GCACACATCTATTGGGACGATGACAAGCGGTACAGTACTAGCCTGAAAAC

GAGACTGACCATAAGCGAGGACTCATCCAAGAATCAGGTGGTACTGACGA

TGACCAACATGGATCCCGTTGATACCGCCACATACTACTGTGCCAGGAAA

GGCTACTATGGCTATTTCGACTATTGGGGACAGGGAACACTCGTCACTGT

GTCCTCT
``` and/or
(b) the nucleotide sequence of SEQ ID NO: 15

```
                                            [SEQ ID NO: 15]
GACATCCAGATGACCCAATCTCCCTCTAGCTTGTCCGCTAGTGTCGGTGA

TAGGGTGACAGTGACATGCAGAGCTAGCCAGAATGTCAACACAGACGTTG

CCTGGTATCAGCAGAAGCCAGGCAAAGCACCCAAAGCCCTCATCTTCTCC

ACGTCATATCTGCAAAGCGGAGTACCTTCCCGGTTTAGTGGGTCTGGGTC

AGGCACTGACTTCACCCTGACCATATCCAGCCTTCAACCGGAAGATTTCG

CGACCTACTACTGTCAGCAGTACAGCAACTATCCTCTGACTTTTGGACAG

GGCACTAAGGTGGAGATTAAGCGT
```

Thus, the nucleic acid molecule of the invention may comprise (a) the nucleotide sequence of SEQ ID NO: 16

[SEQ ID NO: 16]
CAGGTCACACTGAAGGAATCTGGGCCTGCTTTGGTGAAGCCCACTCAGAC

TCTGACACTCACATGCACCTTCTCCGGGTTTAGCCTGTCAACCACCGGTA

TGGGCGTGAGTTGGATTCGCCAACCACCGGGTAAAGCGCTTGAGTGGCTT

GCACACATCTATTGGGACGATGACAAGCGGTACAGTACTAGCCTGAAAAC

GAGACTGACCATAAGCGAGGACTCATCCAAGAATCAGGTGGTACTGACGA

TGACCAACATGGATCCCGTTGATACCGCCACATACTACTGTGCCAGGAAA

GGCTACTATGGCTATTTCGACTATTGGGGACAGGGAACACTCGTCACTGT

GTCCTCTGCTAGCACCAAGGGCCCATCGGTCTTCCCCCTGGCACCCTCCT

CCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAGT

TGAGCCCAAATCTTGTGACAAAACTCACACATGCCCACCGTGCCCAGCAC

CTGAACTCCTGGGGGACCGTCAGTCTTCCTCTTCCCCCCAAAACCCAAG

GACACCCTCATGATCTCCCGGACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAGC

ACGTACCGTGTGGTCAGCGTCCTCACCGTCCTGCACCAGGACTGGCTGAA

TGGCAAGGAGTACAAGTGCAAGGTCTCCAACAAAGCCCTCCCAGCCCCA

TCGAGAAAACCATCTCCAAAGCCAAAGGGCAGCCCCGAGAACCACAGGTG

TACACCCTGCCCCCATCCCGGGAGGAGATGACCAAGAACCAGGTCAGCCT

GACCTGCCTGGTCAAAGGCTTCTATCCCAGCGACATCGCCGTGGAGTGGG

AGAGCAATGGGCAGCCGGAGAACAACTACAAGACCACGCCTCCCGTGCTG

GACTCCGACGGCTCCTTCTTCCTCTACAGCAAGCTCACCGTGGACAAGAG

CAGGTGGCAGCAGGGGAACGTCTTCTCATGCTCCGTGATGCATGAGGCTC

TGCACAACCACTACACGCAGAAGAGCCTCTCCCTGTCTCCGGGTAAATGA and/or
(b) the nucleotide sequence of SEQ ID NO: 17

[SEQ ID NO: 17]
GACATCCAGATGACCCAATCTCCCTCTAGCTTGTCCGCTAGTGTCGGTGA

TAGGGTGACAGTGACATGCAGAGCTAGCCAGAATGTCAACACAGACGTTG

CCTGGTATCAGCAGAAGCCAGGCAAAGCACCCAAAGCCCTCATCTTCTCC

ACGTCATATCTGCAAAGCGGAGTACCTTCCCGGTTTAGTGGGTCGGGTC

AGGCACTGACTTCACCCTGACCATATCCAGCCTTCAACCGGAAGATTTCG

CGACCTACTACTGTCAGCAGTACAGCAACTATCCTCTGACTTTTGGACAG

GGCACTAAGGTGGAGATTAAGCGTACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

-continued
GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGT

Also included within the scope of the invention are the following:

(a) a third aspect of the invention provides a vector (such as an expression vector) comprising a nucleic acid molecule according to the second aspect of the invention;

(b) a fourth aspect of the invention provides a host cell (such as a mammalian cell, e.g. human cell) comprising a nucleic acid molecule according to the second aspect of the invention or a vector according to the third aspect of the invention; and (c) a fifth aspect of the invention provides a method of making an antibody polypeptide according to the first aspect of the invention comprising culturing a population of host cells according to the fourth aspect of the invention under conditions in which said polypeptide is expressed, and isolating the polypeptide therefrom.

A sixth aspect of the invention provides a pharmaceutical composition comprising a pharmaceutically effective amount of an antibody polypeptide of the first aspect of the invention and a pharmaceutically-acceptable diluent, carrier or excipient.

Additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g., through freeze drying, spray drying, spray cooling, or through use of particle formation from supercritical particle formation.

By "pharmaceutically acceptable" we mean a non-toxic material that does not decrease the effectiveness of the kallikrein protein-binding activity of the agent of the invention. Such pharmaceutically acceptable buffers, carriers or excipients are well-known in the art (see *Remington's Pharmaceutical Sciences,* 18th edition, A. R Gennaro, Ed., Mack Publishing Company (1990) and *Handbook of Pharmaceutical Excipients,* 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the agent of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The antibody polypeptides of the invention may be formulated into any type of pharmaceutical composition known in the art to be suitable for the delivery thereof.

In one embodiment, the pharmaceutical compositions of the invention may be in the form of a liposome, in which the antibody polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the antibody polypeptides may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active antibody polypeptide. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, and rectal. Also administration from implants is possible. Infusion may be a desired route because of the potentially high cytotoxicity of the administered agent.

In one embodiment, the pharmaceutical compositions are administered parenterally, for example, intravenously, intracerebroventricularly, intraarticularly, intra-arterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (for example, to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g., intravenous administration or local administration to a tumour in a patient (for example, intra-tumourally or peri-tumourally).

The pharmaceutical compositions will be administered to a patient in a pharmaceutically effective dose, i.e. a therapeutically effective absorbed dose of the therapeutic radionuclide.

In the context of therapeutic use of the antibody polypeptides of the invention, a 'pharmaceutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e., a carrier or administration vehicle. Further, it is intended to mean an amount sufficient to reduce and/or prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical worker based on patient characteristics, such as age, weight, sex, condition, complications, other diseases, etc., as is well known in the art (see Example 6 below). The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

In the context of diagnostic use of the antibody polypeptides of the invention, a 'pharmaceutically effective amount', or 'effective amount', or 'diagnostically effective', as used herein, refers to that amount which provides a detectable signal for in vivo imaging purposes.

The antibody polypeptides of the invention can be formulated at various concentrations, depending on the efficacy/toxicity of the compound being used. The formulation may comprises the polypeptide at a concentration of between 0.1 µM and 1 mM, between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM and about 500 µM.

Typically, the therapeutic dose of the antibody polypeptide (with or without a therapeutic moiety) in a human patient will be in the range of 100 µg to 700 mg per administration (based on a body weight of 70 kg). For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

It will be appreciated by persons skilled in the art that the pharmaceutical compositions of the invention may be administered alone or in combination with other therapeutic agents used in the treatment of a prostate cancer, or before, after or at the same time as the treatment of the patient with other therapeutic modalities for the treatment of prostate cancer, such as other therapeutic antibodies, surgery (e.g., radical prostatectomy), radionuclide therapy, brachytherapy, external beam radiation therapy, high-intensity focused ultrasound (HIFU), chemotherapy, oral chemotherapeutic drugs, cryosurgery (freezing the tumour), hormonal therapy (such as antiandrogen therapy), castration or combinations of the foregoing.

A seventh aspect of the invention provides a kit comprising an antibody polypeptide according to the first aspect of the invention or a pharmaceutical composition according to the sixth aspect of the invention, together with instructions for use of the same as described herein.

An eighth aspect of the invention provides an antibody polypeptide according to the first aspect of the invention for use in medicine.

A ninth aspect of the invention provides an antibody polypeptide according to the first aspect of the invention for use in the treatment and/or diagnosis of prostate cancer.

A tenth aspect of the invention provides a method of treatment of prostate cancer in a subject, the method comprising administering to the subject a therapeutically effective amount of a antibody polypeptide according to the first aspect of the invention.

By 'treatment' we include both therapeutic and prophylactic treatment of the patient. The term 'prophylactic' is used to encompass the use of an agent, or formulation thereof, as described herein which either prevents or reduces the likelihood of prostate cancer, or the spread, dissemination, or metastasis of localised prostate cancer in a patient or subject. The term 'prophylactic' also encompasses the use of an agent, or formulation thereof, as described herein to prevent recurrence of prostate cancer in a patient who has previously been treated for prostate cancer.

An eleventh aspect of the invention provides a method of diagnosis of prostate cancer in a subject, the method comprising administering to the subject a diagnostically effective amount of a antibody polypeptide according to the first aspect of the invention.

By "diagnosis" we include the detection of prostate cancer cells, either in vivo (i.e. within the body of a patient) or ex vivo (i.e. within a tissue or cell sample removed from the body of a patient).

The prostate cancer to be treated or diagnosed may be localised to the prostate, or may be a non-localised (that is, disseminated) prostate cancer. Prostate cancer localised to the prostate may, for example, be classified as clinical T1 or T2 cancers according to the TNM system (abbreviated from Tumor/Nodes/Metastases) whereas non-localised/disseminated prostate cancer may, for example, be classified as clinical T3 or T4 cancers.

The prostate cancer to be treated or diagnosed may be a metastatic prostate cancer. Metastasis refers to the spread of a cancer from its original location to other sites in the body. For example, the metastatic prostate cancer to be treated or diagnosed may be a metastases present in the lymphatic system; in bone (including spine, vertebrae, pelvis, ribs); metastasis within pelvis, rectum, bladder, or urethra. Metastases present at other less common locations can also be treated with the present invention. The metastases may be micrometastases. Micrometastase is a form of metastases in which the newly formed tumors are generally too small to be detected, or detected with difficulty. For example, the present invention provides the skilled person with means to treat single cancer cells or cell clusters, even if the presence of such cells or clusters are not possible to diagnose but exist, for example as occult disseminated disease.

Accordingly, it is anticipated that a particularly important technical advantage of the treatment provided by the present invention compared to the prior art treatments of prostate cancer is the enhanced efficacy in treatment of disseminated and/or metastatic (including micrometastatic) prostate cancer.

Thus, in one embodiment, the invention provides antibody polypeptides and methods for preventing or treatment metastasis of a primary prostate tumour.

Prostate cancer tends to develop in men over the age of fifty, more commonly in men over 60, 65 or 70, and although it is one of the most prevalent types of cancer in men, many never have symptoms, undergo no therapy, and eventually die of other causes. This is because cancer of the prostate is, in most cases, slow-growing, symptom-free, and since men with the condition are older they often die of causes unrelated to the prostate cancer, such as heart/circulatory disease, pneumonia, other unconnected cancers, or old age. About two-thirds of prostate cancer cases are slow growing, the other third more aggressive and fast developing.

Accordingly, the development of effective methods for the treatment and diagnosis of prostate cancer is particularly important for management of more aggressive and fast developing forms of the cancer, particularly in younger patient. Accordingly, in one embodiment, the invention relates to the treatment or diagnosis of prostate cancer in a patient who is less than 90, 85, 80, 75, 70, 65, 60, 55, 50, 45, 40 or less years old at the time of diagnosis of prostate cancer and/or at the time of treatment.

Men who have a first-degree relative (father or brother) with prostate cancer are thought to have twice the risk of developing prostate cancer, and those with two first-degree relatives affected are thought to have a five-fold greater risk compared with men with no family history. Accordingly, the invention may relate to the treatment or diagnose of prostate cancer in a patient that is characterised in that one, two, or more, family members, in particular first-degree family members (such as a father or brother), has been previously been diagnosed with prostate cancer.

The invention also relates to the treatment or diagnosis of prostate cancer in a patient, wherein the prostate cancer to be treated has castration-resistant prostate cancer (CRPC). CRPC may be characterised by typically becoming refractory to hormone treatment after one to three years, and resuming growth despite hormone therapy.

In the medical uses and methods of the invention, the antibody polypeptide is typically injected or infused into the body of the patient. In vivo, the antibody polypeptide then binds to tissues that produce the target antigen, PSA; primarily, prostate cancer cells and metastases thereof. Upon binding, the antibody polypeptide may directly exert a therapeutic effect (e.g. inducing cell death via ADCC, CDC or by virtue of carrying a radioisotope or other cytotoxic moiety). Alternatively, the bound antibody polypeptide may serve as a diagnostic (imaging) tool, which may guide the choice of therapy or aid surgical removal of the cancer cells.

It will be appreciated by persons skilled in the art that the antibody polypeptides of the invention may be used in combination with other therapeutic and/or diagnostic agents/treatment, such as external radiotherapy, surgery, cytostatic and androgen treatments.

The foregoing description focuses on embodiments of the present invention applicable to methods for the treatment and diagnosis of prostatic cancer. However, it will be appreciated that the invention is not limited to such applications but may be useful for post-operative examinations, and examinations during or after radiation, cytostatic, and androgen treatments.

In another embodiment RadioGuided Surgery (RGS) or Image-Guided Surgery (IGS) may be used to identify tracer-labeled antibody polypeptides of the invention during and/or before surgery. Thus, an antibody polypeptide comprising a detectable moiety as discussed above may be administered during and/or before surgery. In this embodiment the antibody polypeptides may first be infused. Thereafter, RGS/IGS may be used to identify PSA-producing tissue with a detection instrument sensitive to the detectable moiety, during or before surgery. The detectable moiety may, for example, be a radiation emitting or magnetic-sensitive detectable moiety; it may, for example, be an emitter of Cerenkov radiation and/or Bremsstrahlung; it may be a fluorescent label and/or a magnetic or magnetizable label. Accordingly, the RGS/IGS according to the present invention may, for example, be a method that is based on the detection of optical, Cerenkov, Bremsstrahlung, or beta radiation; the detection of a radionuclide label, and/or may involve magnetometry. RGS is well known to the person skilled in the art as a surgical technique that enables the surgeon to identify tissue "marked" by the detectable moiety.

The visualisations obtained according to the above methods may be combined with other radiological visualisation methods, such as SPECT/PET, computed tomography (CT), ultrasound (US), and magnetic resonance imaging (MRI).

Accordingly, in a further aspect, the present invention also provides antibody polypeptides for use in medicine by administration to a patient with prostate cancer before or during the surgery, such as RadioGuided or Image-Guided Surgery.

A still further aspect of the invention provides an in vitro method for the detection of prostate tumour cells in the blood of a subject, the method comprising:
  (a) providing a sample of blood from a subject to be tested;
  (b) optionally, extracting and/or purifying cells present in the blood sample;
  (c) contacting an antibody polypeptide according to the first aspect of the invention with cells present in the blood sample;
  (d) determining (directly or indirectly) whether the antibody polypeptide binds to free (i.e. uncomplexed) PSA wherein the binding of the antibody polypeptide to free PSA is indicative of the presence of prostate tumour cells in the blood of a subject.

Thus, the method comprises performing an assay to determine whether the blood sample contains free PSA; the presence of free PSA being indicative of the presence of prostate tumour cells in the blood of a subject.

Persons skilled in the art will appreciate that there are many ways to perform such an assay. For example, the immunoassay could be either homogeneous or, more preferably, heterogenous. The assay could also performed in either a competitive or, more preferably, a non-competitive format.

In the case of the heterogeneous, non-competitive assay, an exemplary protocol could be:
  (a) providing a sample of blood from a subject to be tested;
  (b) optionally, extracting and/or purifying cells present in the blood sample;
  (c) contacting a solid phase immobilized antibody polypeptide according to the first aspect of the invention with cells present in the blood sample;
  (d) washing to remove soluble components (not bound to solid surface);
  (e) adding the tracer, i.e. another anti-PSA specific antibody labelled with a reporter molecule/particle;
  (f) washing to remove unbound tracer antibody; and
  (g) detecting the signal from the tracer antibody Between steps b & c or c & d, there should typically be an incubation period to allow the cell to produce soluble PSA, then for it to be detected.

An additional aspect of the invention provides an in vitro method for the detection of prostate tumour cells in the tissue of a subject, the method comprising
  (a) providing a sample of tissue (such an a histological sample) from a subject to be tested;
  (b) optionally, extracting and/or purifying cells present in the tissue sample;
  (c) contacting an antibody polypeptide according to the first aspect of the invention with cells present in the tissue sample;
  (d) determining (directly or indirectly) whether the antibody polypeptide binds to free (i.e. uncomplexed) PSA
wherein the binding of the antibody polypeptide to free PSA is indicative of the presence of prostate tumour cells in the tissue of a subject.

In one embodiment of the above in vitro methods, step (d) is performed by ELISA. However, any assay suitable for detecting antibody-antigen interactions in vitro may be used.

In an additional embodiment, the method further comprises quantification of the prostate tumour cells in the sample.

In a further embodiment of the above in vitro methods, the method is for the diagnosis of prostate cancer in a subject.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

FIG. 1: Representative SPECT/CT images of LNCaP xenografts scanned up to 7 days post-injection of $^{111}$In-DTPA-h5A10.

Figure 2:
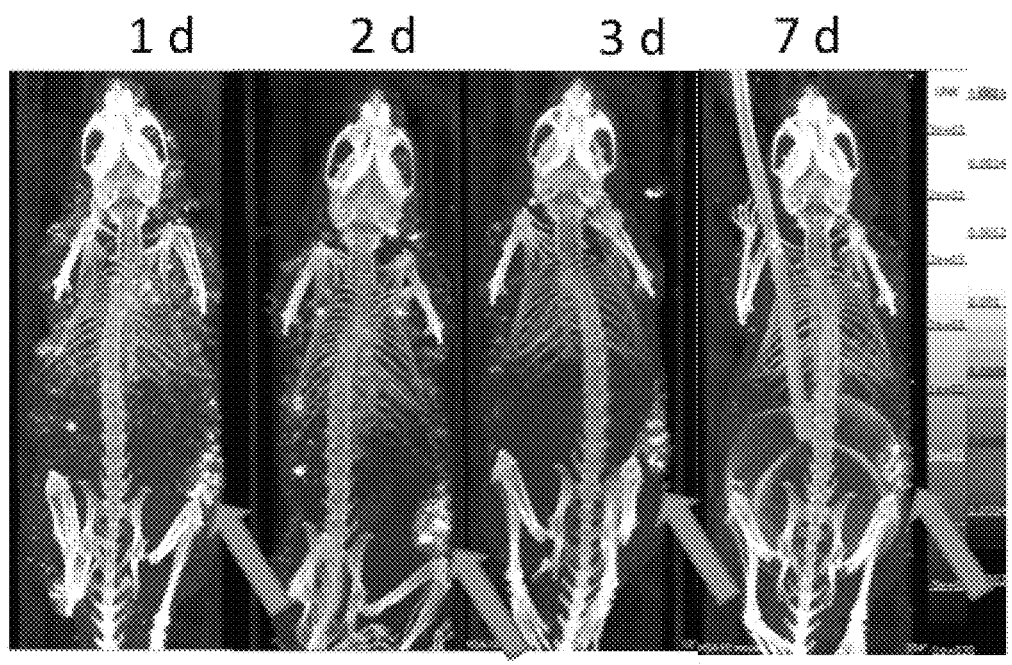

FIG. 2: Representative SPECT/CT images of LNCaP xenografts scanned up to 7 days post-injection of $^{111}$In-DTPA-m5A10.

Figure 3:
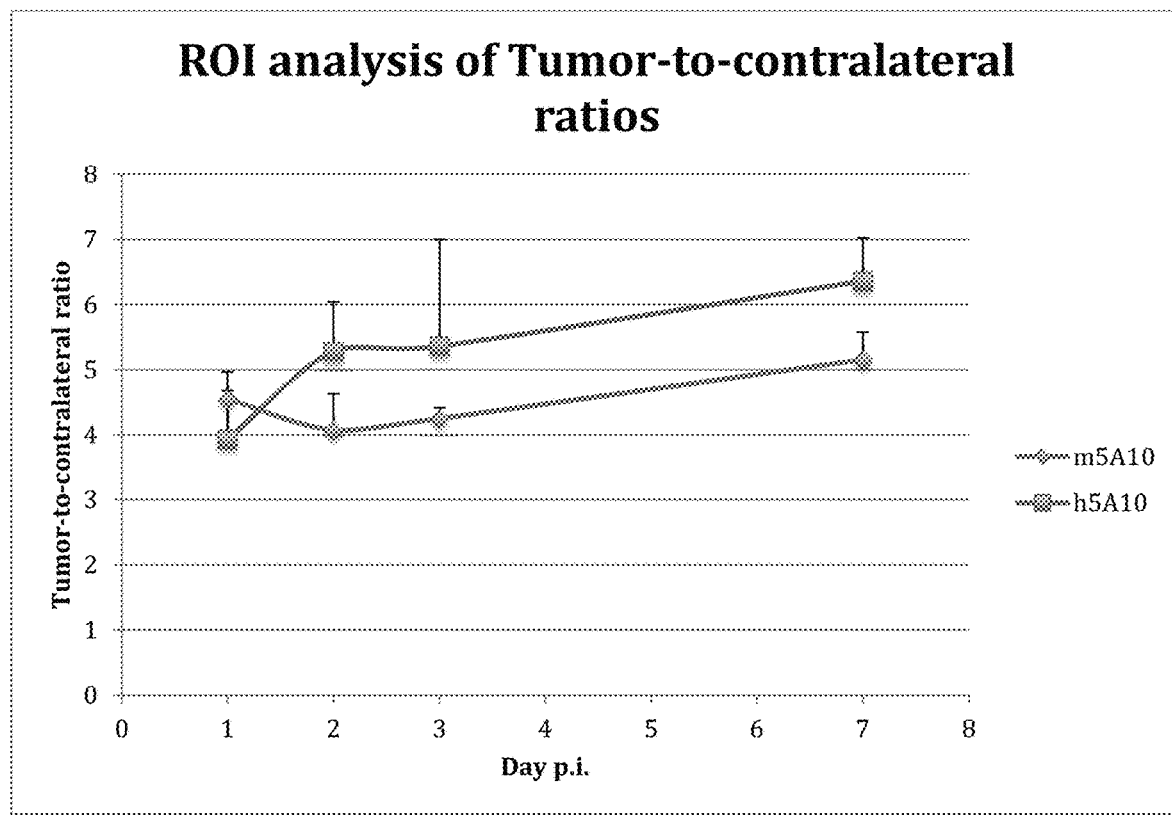

FIG. 3: Analysis of the tumour-to-contralateral ratios of m5A10 and h5A10 in the LNCaP xenograft mouse.

Figure 4:
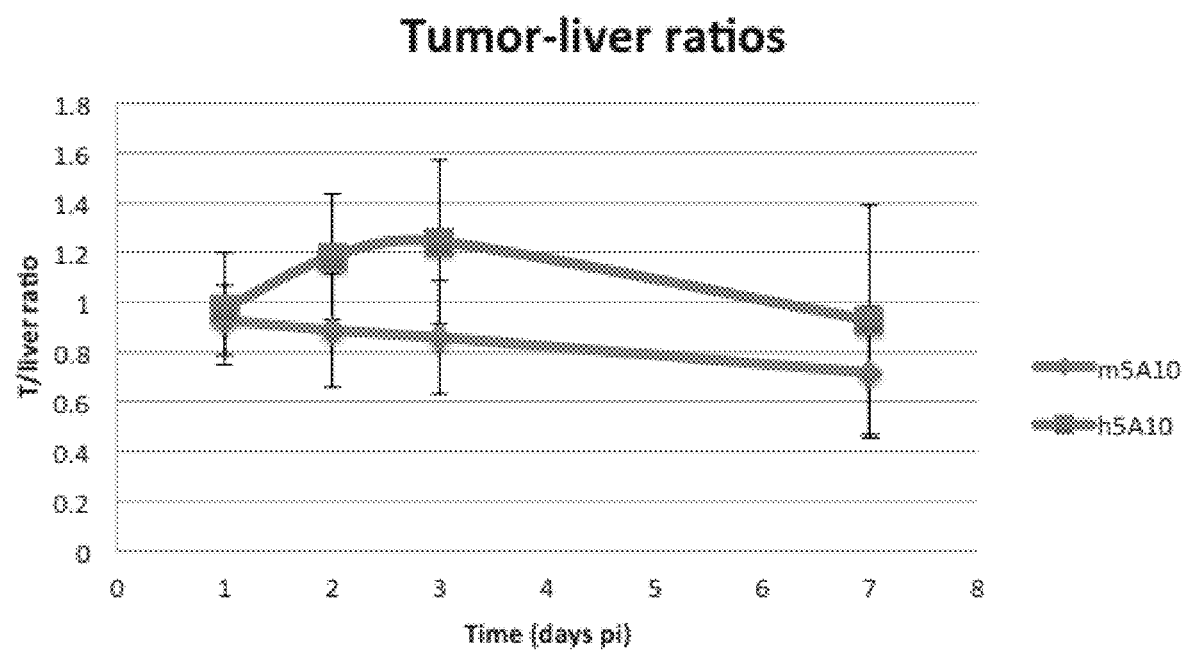

FIG. 4: Analysis of the liver-to-tumour ratios of m5A10 and h5A10 in the LNCaP xenograft mouse.

Figure 5:
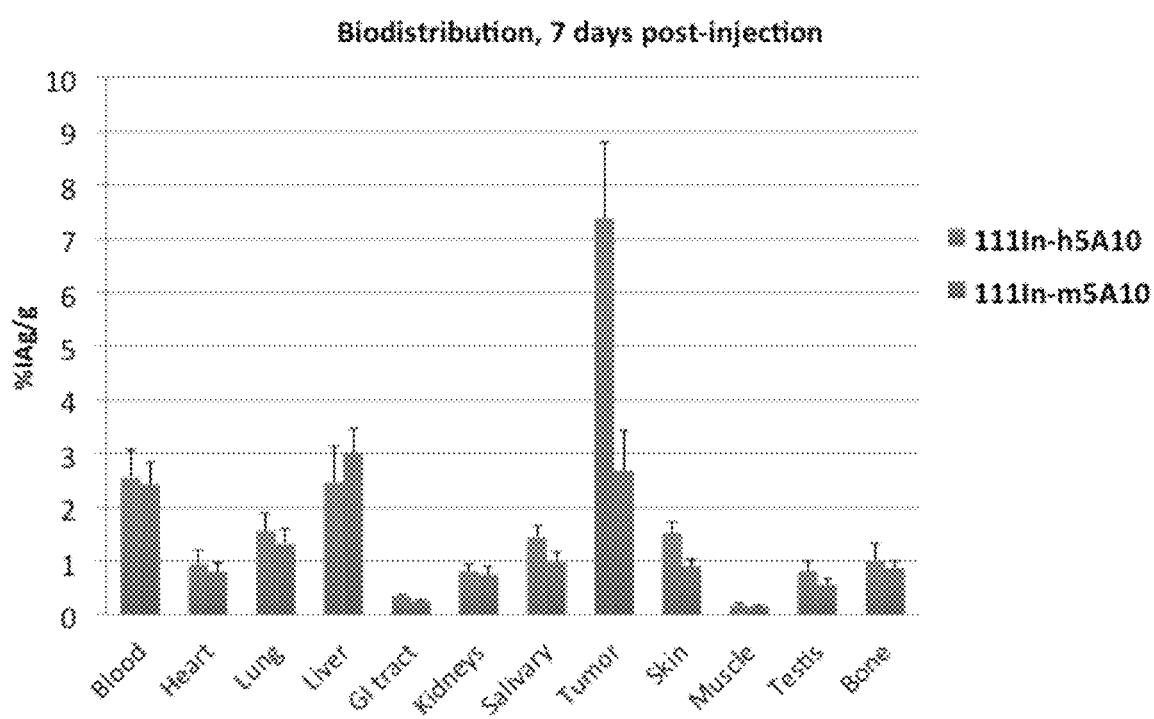

FIG. 5: Biodistribution analysis of $^{111}$In-DTPA-m5A10 and $^{111}$In-DTPA-h5A10 in the LNCaP xenograft mouse.

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1—Cloning of Murine 5A10 Monoclonal Antibody to FAb Format

Reagents

Restriction enzymes were from Fermentas and Promega, alkaline phosphatase from Amersham Pharmacia Biotech and dNTP's and T4 DNA ligase from Fermentas. Primers were from the University of Turku, Department of Biotechnology and from Eurogentec. Qiagen kits were used for DNA purifications.

mRNA Extraction and cDNA Synthesis mRNA was extracted from 5A10 MAb producing hybridoma cells (2E6 cells; Lilja et al, 1991) with Dynal poly-dT magnetic beads according to procedure described by the manufacturer in "Biomagnetic Techniques in Molecular Biology: Technical handbook" (Dynal A. S, 2nd edition, 1995). cDNA synthesis from the mRNA was performed with Super Script enzyme (Gibco BRL): First, the magnetic particles bound with mRNA were incubated at 42° C. for 2 min in a reaction containing 1× reaction buffer, 0.1 M DTT, 2 mM dNTP's and RNase inhibitor (1.5 μl in a 50 μl total reaction volume). Then, 1 μl of Super Script (200 U) was added and the reaction was proceeded 1 hour in 42° C. After cDNA synthesis, the particles and the reaction mixture were separated by magnetic particle collector, the liquid removed, the particles suspended in TE buffer and incubated at 95° C. for 1 min to release the mRNA. After incubation, particle-bound cDNA was collected, mRNA-containing buffer removed, particles washed with TE and finally suspended in 50 μl of TE for storage.

Amplification of the Antibody Genes from cDNA and Cloning

The N-terminal amino acid sequences of the light and heavy chains were determined by Edman degradation method in the University of Turku, Center of Biotechnology sequencing service. The sequences obtained from the light and heavy chain were DIVMTQS [SEQ ID NO: 18] and EVQLVESG [SEQ ID NO: 19], respectively. Based on the N-terminal amino acid sequences, a database search (SwissProt) was performed to identify corresponding nucleotide sequences among the immunoglobulin germline V-genes of mouse. The complementary regions of the forward PCR primers to clone the heavy and light chains were designed based on the search. Reverse primers were designed to bind CH1 and CL, respectively. Primers also contain the restriction enzyme recognition sites needed for cloning (later underlined).

PCR reactions were done in the following conditions (except changing the primers and templates): 125 μM dNTP's, 0.5 μM forward and reverse primers, 1×Pfu reaction buffer and 2.5 U Pfu DNA polymerase (Stratagene). Amplification was done by 30 cycles of 95° C. 30 s, 55° C. 1 min and 72° C. 1 min 30 s.

Light chain was amplified from cDNA with the following primers:

5A10-L
(5'-CCAGCCATGGCTGACATTGTGATGACCCAGTCTCA-3', NcoI
[SEQ ID NO: 20])
and

WO252.
(5'-GCGCCGTCTAGAATTAACACTCATTCCTGTTGAA-3', XbaI
[SEQ ID NO: 21])

The light chain and the vector pComb3 containing the genes of an unrelated Fab (Barbas et al., 1991) were digested with NcoI and XbaI (for the vector, partial digestion with NcoI), purified from agarose gel and ligated. The ligation product was transformed into *E. coli* XL1-Blue to obtain plasmid p5A10-L.

Fd (VH+CH1) chain was amplified with the following primer pair: 5A10-H (5'-CCAGCCATGGCTGAGGTGCAATTGGTGGAGTCTGG-3', NcoI [SEQ ID NO:22]) and WO267 (5'-CTAGACTAGTACAATCCCTGGGCACAATTTTC-3', SpeI [SEQ ID NO:23]). Fd chain was cloned into the vector pComb3 to replace the Fd gene of an another Fab carried by the vector. PCR products and vector were digested with NcoI (partial digestion with NcoI for both the vector and the insert) and SpeI (New England Biolabs), purified from agarose gel and ligated. The ligation product was transformed into *E. coli* XL1-Blue to produce vector p5A10-H.

The 5A10 light chain was digested from the plasmid p5A10-L with SpeI and XbaI and, after gel purification, ligated with the gel purified plasmid p5A10-H also digested with the corresponding enzymes. The ligation product was transformed *E. coli* XL1-Blue to obtain plasmid pComb3-5A10 containing both the light and Fd chain of the Fab 5A10. To remove phage coat protein gene gIIIp fused to the Fd chain, the pComb3-5A10 was further digested with SpeI and NheI, self-ligated and transformed into *E. coli* XL1-Blue. The plasmid pComb3-5A10D111 enabled expression of soluble functional Fab 5A10.

REFERENCES

Barbas C F 3rd, Kang A S, Lerner R A, Benkovic S J. (1991) Assembly of combinatorial antibody libraries on phage surfaces: The gene III site. *Proc. Nat. Acad. Sci.*, Vol. 88, pp. 7978-7982
Biomagnetic Techniques in Molecular Biology: Technical handbook. Dynal A. S, 2nd edition, 1995
Lilja H, Christensson A, Dahlén U, Matikainen M T, Nilsson O, Pettersson K, Lövgren T. (1991) Prostate-specific antigen in serum occurs predominantly in complex with alpha 1-antichymotrypsin. *Clin Chem.* 37(9):1618-25

Example 2—Expression and Purification of a Humanised 5A10 Antibody

HEK293 cells were expanded in to a 2 L suspension culture in FreeStyle 293 Expression Medium (Life Technologies). The cell density was on the day for transfection $1 \times 10^6$ cells/ml.

The nucleotide sequences encoding the component heavy or light chains (i.e. SEQ ID NOs: 16 and 17, respectively) were codon-optimized for expression in mammalian cells, synthesized and cloned to IgG expression vectors. The plasmid DNA (expression vector) containing the nucleotide sequences for the heavy and light chains was then mixed with the transfection agent and incubated for 10 min in RT. The DNA-transfection agent-mix was slowly added to cell culture while slowly swirling the flask. The transfected cell culture was then incubated at 37° C., 8% $CO_2$ on an orbital shaker platform rotating at approx. 135 rpm, for seven days.

Culture medium was harvest by centrifugation and filtered through 5 μm, 0.6 μm and 0.22 μm filter systems.

Antibodies were purified by Protein G chromatography and the buffer was changed to PBS pH 7.4 by dialysis; subsequently, the antibodies were concentrated by ultrafiltration.

Concentration was measured by absorbance.

DNA:

| Light chain: p5A10VLhDhk (4300 bp) amount: | 0.35 mg |
| Heavy chain: p5A10VHhDhIgG1 (4900 bp) amount: | 0.60 mg |

The DNA amounts were not optimized.

Transfection agent: proprietary (however, suitable commercially-available transfection agents are readily available, such as Xfect™ Transfection Reagent (Clontech), Lipofectamine (Life Technologies), FuGENE® HD Transfection Reagent (Promega), FreeStyle™ Max Reagent (Invitrogen), DEAE-dextran, polyethylenimine and calcium phosphate).

Overall yield: 15 mg (7.5 mg/L).

Example 3—Characterisation of h5A10: Affinity

Aims of Study

The aim of the study was to investigate the binding kinetics between eight variants of the antibody 5A10 and the antigen PSA by using the technique of Surface Plasmon Resonance (SPR) on a Biacore™ instrument.

In order to investigate the quality of the protein samples (antibodies and antigen), a SDS-PAGE gel was run prior to the SPR experiments.

In a Pre-Study, different parameters were investigated in order to find the appropriate conditions for the experiments in the Study.

In the Study, multiple binding measurements were performed for the eight antibodies and the antigen. From the collected data, the association and dissociation rate constants ($k_{on}$ and $k_{off}$) and the dissociation constants (KD) were calculated and reported here.

Reagents and Instrument Information

Following solutions of the eight antibodies and one antigen were provided by Diaprost AB:
  PSA 169 μg/ml
  m5A10 (141203) 1 mg/ml
  m5A10 (140905) 4 μM
  m5A10-DFO (140905) 4 μM
  m5A10-DOTA (140905) 4 μM
  m5A10-DTPA (140905) 4 μM
  h5A10 (141203) 1 mg/ml
  h5A10-DFO (141203) 2 mg/ml
  h5A10-DTPA (141203) 1 mg/ml
  h5A10-DOTA (141211) 2.5 μM All the samples were aliquoted and kept in −20° C. freezer prior to analysis.

All binding experiments were performed on CM4 chip on a Biacore™ 3000 instrument. The chip and all the reagents needed for activation, immobilization, deactivation, binding and regeneration were purchased from GE Healthcare and used according to the guidelines from the manufacturer.

SDS-PAGE (a) Description of the Experiment

The reagents provided by Diaprost AB were run on a TRIS-Tricine 10-20% acrylamide gel from Novex according to the guidelines from the manufacturer.

Two series of the protein samples, native and reduced, were run simultaneously on the same gel together with a standard sample.

Each sample in the native series contained: 1-1.3 µg of the protein, TRIS-buffer pH 7.4, SDS and loading buffer.

Each sample in the reduced series contained: 1-1.3 µg of the protein, TRIS-buffer pH 7.4, SDS, loading buffer and 0.04% v/v beta2-merkaptoethanol (the reducing agent).

The staining of the gel was performed in commasie brilliant blue solution of acetic acid, ethanol and water with the corresponding proportions of 0.7, 3.0, 6.3.

The destaining of the gel was performed in the solution of acetic acid, ethanol and water with the corresponding proportions of 0.7, 3.0, 6.3.

(b) Results & Conclusions

It is evident from these results that the antibody and antigen samples are of high quality and purity (results not shown).

Affinity Study (a) Two Experiments where Performed in Order to Determine the Affinity of the Interactions Using the Below Described Conditions.

Immobilisation of antigen on a CM4 chip.

Activation of the chip CM4-1 was performed according to manufacturer's guidelines for amine coupling using EDC and NHS mixture.

A solution containing 3.00 µg/ml of the antigen PSA (stock solution of PSA diluted in 10 mM NaAc-buffer pH 3.8) was flown over channels fc2-4 on the chip CM4-1 in order to immobilize the antigen on the chip. Flow rate: 5 µl/min, volume: 200 µl.

| Target RU ≤ $M_w$/10 | $M_w$(PSA) = 30 000 Da | Target RU (PSA) ≤3000 |
|---|---|---|

Channel fc1 was used as a blank.

The following immobilization was achieved in the first experiment:

| fc2 = 1450 RU | fc3 = 850 RU | fc4 = 900 RU |
|---|---|---|

The following immobilization was achieved in the second experiment:

| fc2 = 1325 RU | fc3 = 890 RU | fc4 = 1060 RU |
|---|---|---|

All channels (fc1-4) were blocked by ethanolamine after activation and immobilization.

These data demonstrate that appropriate immobilization was achieved using 3.00 µg/ml of the antigen.

(b) Investigation of the Association Phase

The association phase of the eight antibodies to the chip CM4-1 was followed for 5 minutes when solutions of 4 different concentrations of each antibody (stock solutions diluted in HSP-buffer) were flown over the channels fc2-4 on the chip CM4-1 with a rate of 30 µl/min.

The investigated concentrations for each antibody were: 100, 50, 25, and 12.5 nM.

Additionally association data was obtained from the experiments where the dissociation process was followed for 8 hours.

In total, 3-9 individual association experiments for each antibody were performed.

The signal from the blank, fc1, was subtracted for all the data.

We found that after 5 minutes, we were able to fit the data for the association processes.

(c) Investigation of the Dissociation Phase

The dissociation phase was followed for 8 hours for each of the antibodies.

The signal from the blank, fc1, is subtracted in all the data used in the calculations of the dissociation rate constant.

The data indicate that the dissociation processes are very slow.

(d) Estimation of the Dissociation Rate Constant ($k_{off}$)

The dissociation phase data was fitted and the dissociation rate constants ($k_{off}$) were estimated (see Table 1).

(e) Estimation of the Association Rate Constant ($k_{on}$)

In order to estimate the association rate constants, the dissociation rate constants (Table 1) were used in the fitted equations.

(f) Estimation of the Dissociation Constant ($k_D$)

Dissociation constant ($K_D$) for each of the tested antibodies are shown in Table 1.

TABLE 1

| Antibody | $K_{off}$ ($10^{-6}$ s$^{-1}$) | $K_{on}$ ($10^6$ M$^{-1}$ s$^{-1}$) | $K_D$ ($10^{-11}$ M) |
|---|---|---|---|
| m5A10 (140905) | 6.3 | 0.29 | 2 |
| m5A10 (141203) | 5.4 | 0.25 | 2 |
| hu5A10 (141203) | 4.8 | 0.62 | 1 |
| m5A10-DFO (140905) | 6.6 | 0.29 | 2 |
| h5A10-DFO (141203) | 8.3 | 0.17 | 5 |
| m5A10-DOTA (140905) | 6.3 | 0.28 | 2 |
| h5A10-DOTA (141211) | 11.7 | 0.54 | 2 |
| m5A10-DTPA (140905) | 6.3 | 0.27 | 2 |
| h5A10-DTPA (141203) | 4.8 | 0.39 | 1 |

The dissociation constants ($K_D$) are in the $10^{-11}$ M range for all eight antibodies.

Although not statistically significant, the dissociation constant for the humanised antibody appears to be higher than that of the parent murine antibody.

Conjugation of the humanised antibodies does not appear to affect the affinity since the $K_D$ is not significantly changed.

Summary

The association processes are very fast for all antibodies and the association rate constants ($k_{on}$) are all in the $10^5$ M$^{-1}$ s$^{-1}$ range based on 3-9 experiments for each antibody.

The dissociation processes are very slow and almost in the range of technical limitations of Biacore™. The dissociation rate constants ($k_{off}$) are all in the $10^{-6}$ s$^{-1}$ range based on 3-9 experiments for each antibody.

The dissociation constants ($K_D$) are in the $10^{-11}$ M range for all antibodies.

Example 4—Characterisation of h5A10: Aggregation

Executive Summary

Dynamic light scattering (DLS) studies have been carried out on 6 variants of the IgG in order to study their propensity to aggregate. The DLS results show that all constructs have a reasonable size (200 kDa or slightly above 200 kDa assuming a spherical protein) and little or no aggregation.

Objective

To characterise six IgG constructs with respect to oligomeric state using dynamic light scattering.

Results

Dynamic Light Scattering

Dynamic light scattering was measured at 20° C. in duplicate samples using the Malvern Zetasizer APS equipment. Each sample was measured three times. The HBS-EP buffer (from the customer) was used as control to make sure that the buffer was reasonably free from dust and aggregates. No reliable measurements of aggregates in the HBS-EP buffer could be made, which is good, since the buffer should be free from aggregates. All samples could be reliably measured using the number distribution function. The average radius of the most abundant species was calculated along with the polydispersity of the species. The average mass distribution of this species was also calculated, see Table 2.

TABLE 2

Dynamic light scattering data derived from size distribution

| Construct | Average radius (nm) | Polydispersity (%) | Mass distribution (%) |
|---|---|---|---|
| m5A10-DFO | 6.1 | 22.7 | 100 |
| h5A10-DFO | 6.3 | 10.2 | 98.7 |
| m5A10-DOTA | 6.2 | 24.6 | 100 |
| h5A10-DOTA | 6.4 | 11.3 | 99.1 |
| m5A10-DTPA | 6.2 | 27.5 | 100 |
| h5A10-DTPA | 6.2 | 10.6 | 98.9 |

Polydispersity = Standard deviation of radius/Average radius × 100%

A radius of 5.7 nm corresponds to a molecular weight of about 200 kDa for a protein having a perfect spherical shape. A radius of 6.1 nm corresponds to a molecular weight of about 230 kDa for a protein having a perfect spherical shape. This is reasonably close to the molecular weight of 150 kDa for IgG molecules, which means that most of the samples primarily consist of monomeric and/or dimeric IgG molecules. The reason for not excluding dimers is that light scattering give a rough size estimate based on molecular shape and this makes it difficult to separate monomers and dimers but easy to separate large aggregates from monomers. Small particles below 1 kDa were found in all mouse IgG samples. These particles have been disregarded in table 1, since it is assumed that they belong to a component found in the buffer due to their small size. On the contrary a small fraction of larger aggregates is found in all human IgG but not in the mouse IgG.

Conclusions

Dynamic light scattering shows that all constructs have a reasonable size and little or no aggregation. The size distributions for all six constructs are overlapping. Surprisingly bufferlike particles (<1 kDa) are found in all mouse IgG samples, whereas larger aggregates are found in the human IgG samples only.

Example 5—Characterisation of h5A10: In Vivo Biodistribution

This study compares in vivo biodistribution of murine 5A10 and human 5A10 when labeled with $^{111}$In.

Material and Methods

A humanised counterpart antibody, h5A10, was produced as described below.

Antibodies: The exemplary humanised monoclonal antibody 5A10 (IgG1/kappa, transient expressed in HEK 293 cells; see Example 2), comprising a heavy chain according to SEQ ID NO:12 and a light chain according to SEQ ID NO:13, was provided by Innovagen AB, Lund (lot no 90475.33, conc 1.0 mg/ml in PBS, pH 7.4). A non-specific IgG antibody was utilised as an isotype control (IgG antibody from mouse serum, Sigma 1-8765).

Conjugation and Radiolabelling

Conjugation of CHX-A"-DTPA with 5A10:

Solutions of the murine and humanised 5A10 mAbs in PBS or NaCl was adjusted to pH 9.2 using 0.07 M sodium borate buffer (Sigma Aldrich). The protein solution was then conjugated with chelator CHX-A"-DTPA (Macrocyclics, USA) in a molar ratio of 3:1 chelator to antibody at 40° C. for 4 h. The reaction was terminated and CHX-A"-DTPA-11B6 (DTPA-11B6) was separated from free chelate by size-exclusion chromatography on a NAP-5 column (GE Healthcare), equilibrated with 20 ml 0.2 M ammonium acetate buffer, pH 5.5. The conjugated 5A10 antibodies were eluted with 1 ml ammonium acetate buffer and aliquoted samples of 200 uL were stored at −20° C.

Radiolabeling of DTPA-5A10:

Murine and humanised DTPA-5A10, in ammonium acetate buffer pH 5.5 was mixed with a predetermined amount of $^{111}$InCl$_3$ (Mallinkrodt Medical, Dublin, Ireland). After incubation at room temperature for 2 h, the labeling was terminated and purified on a NAP-5 column, equilibrated with PBS (Thermo Scientific, USA). Labelling efficiency and kinetics were monitored by instant thin-layer chromatography (ITLC) (Biodex, Shirley, N.Y., USA) eluted with 0.2 M citric acid (Sigma Aldrich). In this system, the radiolabelled conjugate remains at the origin line, while free $^{111}$In. The radioactive distribution was determined using a Cyclone Storage Phosphor System with Optiquant quantification software (Perkin Elmer; Waltham, Mass., USA)

Animal Studies

For in vivo studies, the prostate carcinoma cell lines LNCaP expressing hK2 (ATCC, Manassas, Va., USA) was used. Cells were cultured in RPMI 1640 medium (Thermo Scientific) supplemented with 10% fetal bovine serum and PEST (penicillin 100 IU/ml and 100 μg/ml streptomycin) from Thermo Scientific. The cells were maintained at 37° C. in a humidified incubator with 5% CO$_2$ and were detached with trypsin-EDTA solution (0.25% trypsin, 0.02% EDTA buffer, Thermo Scientific). Matrigel™ matrix (BD-Biosciences, San-Jose, Calif., USA) was used when xenografting LNCaP cells.

All animal experiments were performed in accordance with national legislation on laboratory animals' protection and with the approval of the Ethics Committee for Animal Research (Lund University, Sweden)

Male immunodeficient nude mice, NMRI-Nu, 6-8 wk old (Janvier Labs, France), were used for this study. All mice were s.c. xenografted with LNCaP cells on their left flank, 5-6 million cells, in 100 μl growth medium and 100 μl Matrigel. The xenografts were allowed to grow for 6-8 weeks.

SPECT/CT Imaging Studies

SPECT/CT imaging studies were performed on $^{111}$In-DTPA-h5A10 and $^{111}$In-DTPA-m5A10. Animals were anaesthetized with 2% to 3% isoflurane gas (Baxter; Deerfield, Ill., USA) during imaging. NMRI-nu mice with s.c. LNCaP xenografts were intravenously injected in tail vein with $^{111}$In-DTPA-h5A10 (n=4) or $^{111}$In-DTPA-h5A10 (n=4) with approximately 13-15 MBq, 50 ug of mAb in 100 uL PBS. Animals were imaged for 1 h by using a preclinical SPECT/CT scanner (NanoSPECT/CT Plus, Bioscan; Washington, D.C., USA) with the NSP-106 multi-pinhole mouse collimator. Imaging was performed 1, 2, 3 and 7 days post-injection. SPECT data were reconstructed using HiSPECT software (SciVis; Goettingen, Germany). CT imaging was done before each whole-body SPECT. SPECT/CT images were analysed using InVivoScope 2.0 software (inviCRO; Boston, Mass., USA), and region-of-interest, ROIs, were drawn using the CT image as anatomical reference.

Biodistribution Studies

Biodistribution studies were performed on both $^{111}$In-DTPA-h5A10 and $^{111}$In-DTPA-m5A10. Groups of animals (n=12) of mice were intravenously injected with $^{111}$In-DTPA-h5A10 (approximately 3-4 MBq, 50 ug mAb in 100 uL PBS) or $^{111}$In-DTPA-m5A10 (3-4 MBq, 50 ug mAb in 100 uL PBS). The animals were sacrificed 7 days p.i. and organs of interest were collected and analysed with an automated NaI(Tl) well-counter with a 3-inch NaI (Tl) detector (1480 WIZARD, Wallac Oy, Turku, Finland).

The tissue uptake value, expressed as percent injected dose per gram tissue (% IA/g), was calculated as:

% IA/g=(tissue radioactivity/injected radioactivity)/ organ weight×100 wherein for iv injections:

Injected radioactivity = Radioactivity in the syringe

—radioactivity left in used syringe

—radioactivity in tail

The organs were also weighed following dissection. Data were corrected for background and physical decay.

Results

SPECT/CT Imaging

Representative SPECT/CT images of LNCaP xenografts scanned up to 7 days post-injection of $^{111}$In-DTPA-h5A10 and $^{111}$In-DTPA-m5A10 are shown in FIGS. 1 and 2. The activity rapidly accumulates in the LNCaP tumour within by 24 hours, and the radioactivity remains high at 7 days post-injection. High accumulation of activity was also detected in the liver. The ROI analysis showed that the ratio of tumour to soft tissue of the contralateral leg was 5.2±0.84 for $^{111}$In-DTPA-m5A10 and 6.4±1.3 for $^{111}$In-DTPA-h5A10 at 7 days p.i.

Biodistribution

To more thoroughly investigate the activity accumulation in different organs, an ex vivo biodistribution was performed in a larger number of animals (n=12 per antibody).

Tumour to contralateral ratios of $^{111}$In-DTPA-m5A10 and $^{111}$In-DTPA-h5A10 over time are shown in FIG. 3. Unexpectedly, this ratio was observed to be markedly higher for the humanised antibody than for the 'parent' murine antibody.

Tumour to liver ratios of $^{111}$In-DTPA-m5A10 and $^{111}$In-DTPA-h5A10 over time are shown in FIG. 4. Again, unexpectedly, this ratio was observed to be markedly higher for the humanised antibody than for the 'parent' murine antibody.

The biodistribution data of $^{111}$In-DTPA-m5A10 and $^{111}$In-DTPA-h5A10 is shown in FIG. 5.

The biodistribution for the murine and humanized 5A10 in NMRI mice with LNCaP xenografts showed a high tumor accumulation at 7 days while accumulation in other organs, such as bone, muscle were much lower.

Comparison of the biodistribution data for humanised $^{111}$In-DTPA-h5A10 with that for the parent murine antibody ($^{111}$In-DTPA-m5A10) revealed an unexpected and advantageous difference. The tumor accumulation was significantly much higher for the humanized than for the murine, with 7.4±1.4% IA/g for h5A10 compared to 2.7±0.75% IA/g for m5A10 (p<0.001) at 7 days p.i. (FIG. 6). Accumulation of radioactivity in other organs was approximately on the same level for both antibodies, making tumor-to-organ ratios much higher for the humanized h5A10 than for the parent murine m5A10 (Table 3)

TABLE 3

| Tumor-to-organ ratios | | |
|---|---|---|
| | h5A10 | m5A10 |
| Blood | 2.9 | 1.1 |
| Heart | 7.9 | 3.4 |
| Lung | 4.7 | 2.0 |
| Liver | 3.0 | 0.9 |
| GI tract | 21.7 | 10.8 |
| Kidneys | 9.1 | 3.6 |
| Salivary | 5.1 | 2.7 |
| Skin | 4.9 | 3.0 |
| Muscle | 44.2 | 17.6 |
| Testis | 9.1 | 4.8 |
| Bone | 7.3 | 3.1 |

Conclusions and Discussion

The results of this study demonstrate the following:

the humanised 5A10 antibody, $^{111}$In-h5A10, effectively targets prostate tumours in vivo;

the humanised h5A10 antibody exhibits an unexpectedly better tumor accumulation than its murine antibody and the humanised h5A10 antibody provides better imaging contrast (as shown with higher tumor-to-organ ratios) than the murine antibody Taken together, these findings provide compelling evidence of the better targeting properties of humanised 5A10 antibodies in the diagnosis and likely better therapeutic efficacy in the treatment of prostate cancer.

Example 6—Radionuclide Therapy Dosimetry Planning and Treatment of Prostate Cancer in a Patient For radionuclide therapy (RNT), the radiation source is distributed in the whole and the radioactivity is normally administered systemically as a radiopharmaceutical. The radioactivity distribution depends on the amount of radiopharmaceutical that accumulates over time in different tissues, something which varies between patients (1).

RNT treatment should be based on a prescribed absorbed dose (2). Then first one should perform a pre-therapy study using a tracer amount of the radiopharmaceutical, and determine the tumor and organ absorbed doses. Usually, this information is expressed as a factor describing the organ absorbed dose per unit administered activity, in units of mGy/MBq; $D^P_T(organ)$.

If the therapeutic administration is then given under similar conditions, this factor can be used to determine the activity that needs to be administered in order to deliver a prescribed absorbed dose to a given organ, tissue or tumor (4,6).

In the case of prostate cancer treatment with radiolabelled h5A10 antibodies, a pre-therapy study should be based on $^{111}$In imaging with $^{111}$In-h5A10. $^{111}$In is best suitable for quantitative (planar/SPECT) imaging when then $^{177}$Lu is to be the therapeutic radionuclide. When then the $D^F{}_T$(organ) is determined the therapy can be given with a therapy activity $A_T$ giving a prescribed therapy effect. During therapy, the activity distribution and corresponding dose rate should be calculated based on imaging to get the actual therapy absorbed dose given to tumor and normal organs, necessary for evaluation of treatment.

In case of therapy where the bone marrow toxicity level is reached as a result of the treatment planning then bone-marrow support is necessary and based on dosimetry calculations for the bone marrow cavity the time for reinfusion of stem cells has to be determined.

In summary, the following treatment scheme should be planned accordingly:

Pre-Therapy Dosimetry Study
1. $^{111}$In-labeled h5A10 (200-300 MBq) injection
2. Blood sampling—activity concentration in blood and plasma determined first week.
3. Imaging (SPECT/Planar) over at least 1 week (3-5 times)
4. Organ Dosimetry based on LundaDose scheme (3) or equivalent program
5. Therapy activity determined limited by specified absorbed dose to radiosensitive organs as bone marrow (2-3 Gy), kidneys (20-30 Gy) and liver (12-36 Gy).

Therapy Including Intra-Therapy Dosimetry
1. $^{177}$Lu-labeled h5A10 administered (based on pretherapy dosimetry)
2. Blood sampling—activity concentration in blood and plasma
3. Imaging over at least 1 week (3-5 times)
4. Organ Dosimetry based on LundaDose scheme (3) or equivalent program=>Verification of prescribed therapy absorbed dose.

Specific Comments on Dosimetry

The cumulated activity is the number of decays that occur in a given region over a period of time. The unit is Bq s, or Bq h. When ionizing radiation travels through matter, it interacts and deposits energy. The energy imparted is the sum of all energy deposits in a given volume. The absorbed dose is the ratio of the energy imparted and the mass of the volume. The unit of absorbed dose is Gray (Gy), 1 Gy equals 1 J/kg.

From the values of the activity in a tissue at different times, the cumulated activity is determined by integration, and the absorbed dose can be determined. Activity measurements are made using planar imaging for whole-organ dosimetry. Quantitative SPECT/CT allows for dosimetry in smaller volumes using voxel-based methods.

From the 3D distribution of activity concentration values, the absorbed dose rate distribution can be calculated using so-called point dose kernels or voxel S values, describing the energy deposition pattern around a point source located in tissue. This method assumes that the anatomical region is homogeneous in terms of density, such as soft tissues within the trunk. For body regions where the density is heterogeneous, as in the lungs, a direct Monte Carlo calculation is preferable. Here, the activity distribution from SPECT or PET is used as input to a Monte Carlo dose calculation code.

REFERENCES

1. Strand S-E, Zanzonico P, Johnson T K. Pharmacokinetic modeling. Med Phys 1993; 20(2):515-27
2. ICRU report nr 67—Dose Specifications in Nuclear Medicine. Adelstein S J, DeLuca P, Feinendegen L E, Green L, Howell R W, Humm J L, Strand S E ICRU; 2002
3. The LundADose Method for Planar Image Activity Quantification and Absorbed-Dose Assessment in Radionuclide Therapy. Sjogreen, K., Ljungberg, M., Wingardh, K., Minarik, D., and Strand, S. E. (2005): Cancer Biother. Radiopharm., 20:92-97
4. Quantitative imaging for clinical dosimetry. Bardies M, Flux G, Lassman M, Monsieurs N, Savolainen S, Strand S-E Nucl Instr and Methods 2006:569:467-471.
5. 177Lu-[DOTA0,Tyr3] octreotate therapy in patients with disseminated neuroendocrine tumors: Analysis of dosimetry with impact on future therapeutic strategy. Garkavij Michael, Nickel Mattias, Sjögreen-Gleisner Katarina, Ljungberg Michael, Ohlsson Tomas, Wingårdh Karin, Strand Sven-Erik, Tennvall Jan. Cancer 2010: 116(4 Suppl):1084-92.
6. Dosimetry in patients with B-cell lymphoma treated with [(90)Y]ibritumomab tiuxetan or [(131)I]tositumomab Sjögreen-Gleisner K., Dewaraja Y K., Chisea C., Tennvall J., Lindén O., Strand S E, Ljungberg M. Q J Nucl Med Mol Imaging, 2011 April; 55(2):126-54.

The invention claimed is:

1. An antibody polypeptide with binding specificity for prostate specific antigen (PSA),
wherein the antibody polypeptide comprises
(a) a heavy chain variable region comprising the amino acid sequences of SEQ ID NO:1 and SEQ ID NO:2 and SEQ ID NO:3; and
(b) a light chain variable region comprising the amino acid sequences of SEQ ID NO:4 and SEQ ID NO:5 and SEQ ID NO:6
wherein the heavy chain variable region and light chain variable region comprise framework amino acid sequences from one or more human antibodies, and
wherein the PSA is human PSA consisting of the amino acid sequence of SEQ ID NO: 7 or is a mature, active form of human PSA consisting of the amino acid sequence of SEQ ID NO: 24.

2. An antibody polypeptide according to claim 1 comprising or consisting of an intact antibody or an antigen-binding fragment selected from the group consisting of Fv fragments, single chain Fv fragments, disulphide-bonded Fv fragments, Fab fragments, Fab' fragments and F(ab)₂ fragments.

3. An antibody polypeptide according to claim 1 comprising a heavy chain variable region which comprises or consists of the amino acid sequence of SEQ ID NO: 8 and/or a light chain variable region which comprises or consists of the amino acid sequence of SEQ ID NO: 9.

4. An antibody polypeptide according to claim 1 further comprising: a) a heavy chain constant region, or part thereof, optionally wherein the heavy chain constant region is of an immunoglobulin subtype selected from the group consisting of IgG1, IgG2, IgG3 and IgG4; and/or b) a light chain constant region, or part thereof, optionally wherein the light chain constant region is of a kappa or lambda light chain.

5. An antibody polypeptide according to claim 1 comprising a heavy chain constant region which comprises or consists of the amino acid sequence of SEQ ID NO: 10 and/or a light chain constant region which comprises or consists of the amino acid sequence of SEQ ID NO: 11.

6. An antibody polypeptide according to claim 1 comprising a heavy chain which comprises or consists of the amino acid sequence of SEQ ID NO: 12 and/or a light chain which comprises or consists of the amino acid sequence of SEQ ID NO: 13.

7. An antibody polypeptide according to claim 1 wherein the antibody polypeptide is linked, directly or indirectly, to a therapeutic moiety.

8. An antibody polypeptide according to claim 7 wherein the therapeutic moiety is a cytotoxic moiety that comprises or consists of one or more radioisotopes.

9. An antibody polypeptide according to claim 7 wherein the therapeutic moiety is a cytotoxic moiety that comprises or consists of one or more cytotoxic drugs.

10. An antibody polypeptide according to claim 1 wherein the antibody polypeptide further comprises a detectable moiety.

11. An antibody polypeptide according to claim 10 wherein the detectable moiety comprises or consists of a radioisotope.

12. An antibody polypeptide according to claim 7 wherein the therapeutic moiety is joined to the antibody polypeptide indirectly, via a linking moiety.

13. An antibody polypeptide according to claim 12 wherein the linking moiety is a chelator, which is deferoxamine (DFO).

14. A method for the treatment of prostate cancer which expresses prostate specific antigen (PSA) in a human patient, the method comprising the step of administering to a human patient having said cancer a therapeutically effective amount of an antibody polypeptide according to claim 1, wherein said prostate cancer expresses PSA, and wherein the antibody polypeptide comprises an Fc-region and induces antibody-dependent cell-mediated cytotoxicity (ADCC) or complement-dependent cytotoxicity (CDC).

15. A method according to claim 14 wherein the prostate cancer to be treated is non-localised prostate cancer.

16. A method according to claim 15 wherein the prostate cancer to be treated is metastatic prostate cancer, optionally micrometastatic prostate cancer.

17. A method according to claim 16 wherein the metastatic prostate cancer to be treated is metastases of the lymph system; metastases of the bone; and/or metastases within pelvis, rectum, bladder, and/or urethra.

18. A method according to claim 14 wherein the prostate cancer to be treated is castration-resistant prostate cancer (CRPC).

19. An antibody polypeptide according to claim 10 wherein the detectable moiety is joined to the antibody polypeptide indirectly, via a linking moiety.

20. An antibody polypeptide according to claim 19 wherein the linking moiety is a chelator, which is deferoxamine (DFO).

21. A method for the treatment of prostate cancer which expresses prostate specific antigen (PSA) in a human patient, the method comprising the step of administering to a human patient having said cancer a therapeutically effective amount of an antibody polypeptide according to claim 7.

22. A method according to claim 17, wherein the metastases of the bone are of the spine, vertebrae, pelvis, and/or ribs.

* * * * *

UNITED STATES PATENT AND TRADEMARK OFFICE
CERTIFICATE OF CORRECTION

| | | |
|---|---|---|
| PATENT NO. | : 11,332,543 B2 | Page 1 of 1 |
| APPLICATION NO. | : 15/761260 | |
| DATED | : May 17, 2022 | |
| INVENTOR(S) | : Amanda Thuy Tran et al. | |

It is certified that error appears in the above-identified patent and that said Letters Patent is hereby corrected as shown below:

On the Title Page

At Item (72), please delete:
"Vanhalinnna (SE)"

And insert therefor:
--Vanhalinna (FI)--

Signed and Sealed this
Sixteenth Day of August, 2022

Katherine Kelly Vidal
*Director of the United States Patent and Trademark Office*